United States Patent
Soderberg et al.

(10) Patent No.: US 8,752,220 B2
(45) Date of Patent: Jun. 17, 2014

(54) SYSTEMS FOR PATIENT SUPPORT, MONITORING AND TREATMENT

(75) Inventors: Peter H. Soderberg, Boca Grande, FL (US); Christopher R. O'Keefe, Batesville, IN (US); Timothy A. Stanley, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 19 days.

(21) Appl. No.: 12/830,497

(22) Filed: Jul. 6, 2010

(65) Prior Publication Data

US 2011/0030141 A1   Feb. 10, 2011

Related U.S. Application Data

(60) Provisional application No. 61/224,851, filed on Jul. 10, 2009, provisional application No. 61/225,920, filed on Jul. 15, 2009.

(51) Int. Cl.
*A61G 7/015* (2006.01)

(52) U.S. Cl.
USPC ............... 5/600; 5/424; 5/425; 5/426; 5/427; 5/428; 5/429; 5/430

(58) Field of Classification Search
USPC ............................................ 5/600, 424–430
See application file for complete search history.

(56) References Cited

U.S. PATENT DOCUMENTS

| | | | |
|---|---|---|---|
| 2,194,809 A | 3/1940 | Powell, Jr. | |
| 3,325,799 A | 6/1967 | Farris | |
| 3,631,438 A | 12/1971 | Lewin | |
| 3,644,950 A | 2/1972 | Lindsay, Jr. | |
| 3,727,606 A | 4/1973 | Sielaff | |
| 3,836,900 A | 9/1974 | Mansfield | |
| 4,146,885 A | 3/1979 | Lawson, Jr. | |
| 4,183,015 A * | 1/1980 | Drew et al. | 340/4.11 |
| 4,195,287 A | 3/1980 | McCoy et al. | |
| 4,245,651 A | 1/1981 | Frost | |
| 4,320,766 A | 3/1982 | Alihanka et al. | |
| 4,481,686 A | 11/1984 | Lacoste | |
| 4,483,029 A | 11/1984 | Paul | |

(Continued)

FOREIGN PATENT DOCUMENTS

EP   3 417 908 A1   2/2012
JP   6315424   11/1994

OTHER PUBLICATIONS

European Search Report for EP 10 25 1235 dated Mar. 5, 2012.

(Continued)

*Primary Examiner* — William Kelleher
(74) *Attorney, Agent, or Firm* — Barnes & Thornburg LLP

(57) ABSTRACT

A patient support system, such as a bed, stretcher, wheelchair or the like, has an electronic control system and a user interface. The electronic control system and the user interface control bed functions, such as articulation of the head, seat, and leg sections of the bed deck, and control and/or monitor the operation of medical equipment, such as heart rate monitors, blood pressure monitors, thermometers, sequential compression therapy devices, chest wall oscillation devices, respiratory therapy devices, blood oxygen monitors, and the like. In some embodiments, the electronic control system and user interface communicate with patient personal digital devices, such as audio players, computers, and phones. The user interface is on the headboard, footboard, and/or on a siderail of the bed in some embodiments.

20 Claims, 16 Drawing Sheets

(56) References Cited

U.S. PATENT DOCUMENTS

| | | |
|---|---|---|
| 4,485,505 A | 12/1984 | Paul |
| 4,525,885 A | 7/1985 | Hunt et al. |
| 4,559,656 A | 12/1985 | Foster |
| 4,564,965 A | 1/1986 | Goodwin |
| 4,595,023 A | 6/1986 | Bonnet |
| 4,602,643 A | 7/1986 | Dietz |
| 4,637,083 A | 1/1987 | Goodwin |
| 4,657,026 A | 4/1987 | Tagg |
| 4,681,098 A | 7/1987 | Lee |
| 4,694,520 A | 9/1987 | Paul et al. |
| 4,757,825 A | 7/1988 | Diamond |
| 4,799,276 A | 1/1989 | Kadish |
| 4,838,309 A | 6/1989 | Goodwin |
| 4,889,123 A | 12/1989 | Lee |
| 4,889,130 A | 12/1989 | Lee |
| 4,893,633 A | 1/1990 | Lee |
| 4,895,155 A | 1/1990 | Lee |
| 4,928,703 A | 5/1990 | Wong |
| 4,934,468 A | 6/1990 | Koerber, Sr. et al. |
| 4,935,968 A | 6/1990 | Hunt et al. |
| 4,942,635 A | 7/1990 | Hargest et al. |
| 4,949,412 A | 8/1990 | Goode |
| 4,949,414 A | 8/1990 | Thomas et al. |
| 4,971,065 A | 11/1990 | Pearce |
| 5,002,060 A | 3/1991 | Nedivi |
| 5,010,772 A | 4/1991 | Bourland et al. |
| 5,052,067 A | 10/1991 | Thomas et al. |
| 5,057,819 A | 10/1991 | Valenti |
| 5,060,174 A | 10/1991 | Gross |
| 5,117,518 A | 6/1992 | Schild |
| 5,144,284 A | 9/1992 | Hammett |
| 5,170,364 A | 12/1992 | Gross et al. |
| 5,182,826 A | 2/1993 | Thomas et al. |
| 5,184,112 A | 2/1993 | Gusakov |
| 5,197,490 A | 3/1993 | Steiner et al. |
| 5,271,412 A | 12/1993 | Shtalryd et al. |
| 5,283,735 A | 2/1994 | Gross et al. |
| 5,309,921 A | 5/1994 | Kisner et al. |
| 5,448,996 A | 9/1995 | Bellin et al. |
| 5,479,932 A | 1/1996 | Higgins et al. |
| 5,515,865 A | 5/1996 | Scanlon |
| 5,539,942 A | 7/1996 | Melou |
| 5,590,650 A | 1/1997 | Genova |
| 5,664,270 A | 9/1997 | Bell et al. |
| 5,684,460 A | 11/1997 | Scanlon |
| 5,715,548 A | 2/1998 | Weismiler et al. |
| 5,724,990 A | 3/1998 | Ogino |
| 5,794,288 A | 8/1998 | Soltani et al. |
| 5,815,864 A | 10/1998 | Sloop |
| 5,817,146 A | 10/1998 | Augustine |
| 5,825,293 A | 10/1998 | Ahmed et al. |
| 5,829,081 A | 11/1998 | Pearce |
| 5,873,137 A | 2/1999 | Yavets-Chen |
| 5,902,255 A | 5/1999 | Ogino |
| 5,934,280 A | 8/1999 | Viard et al. |
| 5,964,720 A | 10/1999 | Pelz |
| 5,970,789 A | 10/1999 | Meyer et al. |
| 6,009,580 A | 1/2000 | Caminade et al. |
| 6,011,477 A | 1/2000 | Teodorescu et al. |
| 6,014,346 A | 1/2000 | Malone |
| 6,030,347 A | 2/2000 | Nakamura et al. |
| 6,034,526 A | 3/2000 | Montant et al. |
| 6,062,216 A | 5/2000 | Corn |
| 6,079,068 A | 6/2000 | Viard |
| 6,094,762 A | 8/2000 | Viard et al. |
| 6,138,301 A | 10/2000 | Battiston |
| 6,150,941 A | 11/2000 | Geiger et al. |
| 6,212,718 B1 | 4/2001 | Stolpmann et al. |
| 6,280,392 B1 | 8/2001 | Yoshimi et al. |
| 6,315,740 B1 | 11/2001 | Singh |
| 6,375,621 B1 | 4/2002 | Sullivan |
| 6,450,957 B1 | 9/2002 | Yoshimi et al. |
| 6,458,087 B1 | 10/2002 | Al-Rasheed |
| 6,468,234 B1 | 10/2002 | Van der Loos et al. |
| 6,485,441 B2 | 11/2002 | Woodward |
| 6,492,634 B2 | 12/2002 | Marchitto et al. |
| 6,493,568 B1 | 12/2002 | Bell et al. |
| 6,498,234 B1 | 12/2002 | Wallis |
| 6,498,652 B1 | 12/2002 | Varshneya et al. |
| 6,547,743 B2 | 4/2003 | Brydon |
| 6,611,979 B2 | 9/2003 | Welling et al. |
| 6,620,106 B2 | 9/2003 | Mault |
| 6,658,680 B2 | 12/2003 | Osborne et al. |
| 6,721,980 B1 | 4/2004 | Price et al. |
| 6,739,006 B2 | 5/2004 | Borders et al. |
| 6,816,266 B2 | 11/2004 | Varshneya et al. |
| 6,821,258 B2 | 11/2004 | Reed et al. |
| 6,824,513 B2 | 11/2004 | Jansen |
| 6,840,907 B1 | 1/2005 | Brydon |
| 6,899,103 B1 | 5/2005 | Hood et al. |
| 6,917,293 B2 | 7/2005 | Beggs |
| 6,932,774 B2 | 8/2005 | Nakatani et al. |
| 7,962,979 B1 * | 6/2011 | Hime ................ 5/600 |
| 2002/0044059 A1 | 4/2002 | Reeder et al. |
| 2003/0052787 A1 | 3/2003 | Zerhusen et al. |
| 2004/0060111 A1 * | 4/2004 | Alverson .......... 5/425 |
| 2006/0117482 A1 * | 6/2006 | Branson ............ 5/600 |
| 2006/0258964 A1 | 11/2006 | Biondo et al. |
| 2007/0049853 A1 * | 3/2007 | Adams et al. ........ 601/151 |
| 2007/0163043 A1 * | 7/2007 | Lemire et al. ........ 5/600 |
| 2007/0169268 A1 | 7/2007 | Lemire et al. |
| 2007/0180616 A1 | 8/2007 | Newkirk et al. |
| 2008/0000477 A1 * | 1/2008 | Huster et al. .......... 128/204.23 |
| 2008/0060138 A1 | 3/2008 | Price et al. |
| 2008/0172789 A1 | 7/2008 | Elliot et al. |
| 2008/0235872 A1 * | 10/2008 | Newkirk et al. ........ 5/600 |
| 2008/0256706 A1 * | 10/2008 | Larsen ............... 5/425 |
| 2009/0049610 A1 * | 2/2009 | Heimbrock et al. ...... 5/600 |
| 2009/0188731 A1 * | 7/2009 | Zerhusen et al. ........ 180/19.3 |
| 2010/0101022 A1 * | 4/2010 | Riley et al. .......... 5/600 |
| 2011/0231996 A1 * | 9/2011 | Lemire et al. ........ 5/613 |
| 2011/0277242 A1 * | 11/2011 | Dionne et al. ........ 5/611 |

OTHER PUBLICATIONS

Extended European Search Report for Application No. EP 13 179 526.2, dated Oct. 22, 2013, 8 pages.

* cited by examiner

SYSTEMS FOR PATIENT SUPPORT, MONITORING AND TREATMENT

CROSS-REFERENCE TO RELATED APPLICATIONS

This application claims the benefit, under 35 U.S.C. §119 (e), of U.S. Provisional Application No. 61/224,851 which was filed Jul. 10, 2009 and U.S. Provisional Application No. 61/225,920 which was filed Jul. 15, 2009, both of which are hereby incorporated by reference herein.

BACKGROUND

The present disclosure relates generally to patient support systems, such as beds, stretchers, wheelchairs and the like. More particularly, the present disclosure relates to patient supports having therapy delivery devices and/or physiologic monitoring devices integrated therewith.

Patient support systems such as hospital beds conventionally have features adapted to provide comfort to the patient, as well as to assist the caregiver in positioning and transporting the patient. For example, such beds can include articulating sections to allow the patient to be placed in a variety of positions, for comfort of the patient and to assist the caregiver in caring for the patient. Such beds might also include electronic displays to indicate the status of the various features of the bed, such as the brake status, the siderail position, and the bed height. Additionally, such beds can allow for communications with caregivers via audio components.

While such patient support systems can be very useful in assisting caregivers and providing improved safety and comfort to patients, additional medical device and therapy capabilities are oftentimes not included in the conventional patient support systems. Some prior art patient support systems do have therapy and physiologic monitoring devices integrated therein, however. See, for example, U.S. Pat. Nos. 5,664,270; 5,715,548; 6,493,568; 6,899,103; 7,038,588; 7,154,397; 7,343,916; 7,515,059; 7,641,623 and U.S. Patent Application Publication Nos. 20080126132; 20080005838; and 20050190068. However, a need persists for further contributions in this area of technology.

SUMMARY

The present invention comprises one or more of the features recited in the appended claims and/or the following features which, alone or in any combination, may comprise patentable subject matter:

According to this disclosure, a hospital bed may comprise a frame, a plurality of siderails coupled to the frame, a headboard coupled to the frame, and a footboard coupled to the frame. The hospital bed may further comprise a physiologic monitor sensing at least one physiologic parameter of a patient supported by the frame, and a plurality of graphical displays. A first graphical display of the plurality of graphical displays may be included as part of a first siderail of the plurality of siderails and a second graphical display of the plurality of graphical displays may be included as part of one of the headboard and the footboard. Each of the first and second graphical displays may be operable to display the physiologic parameter sensed by the physiologic monitor.

The second graphical display may be included as part of the headboard and may face away from the frame. A third graphical display may be included as part of the headboard. The second graphical display may display data relating to a first physiologic parameter of the patient and the third graphical display may display data relating to a second physiologic parameter of the patient. The second and third graphical displays may be located in spaced-apart, side-by-side relation on the headboard.

In some embodiments, the second graphical display may be included as part of the footboard and may face toward the frame. A third graphical display may be included as part of the footboard as well. The second graphical display may display data relating to a first physiologic parameter of the patient and the third graphical display may display data relating to a second physiologic parameter of the patient. The second and third graphical displays may be located in spaced-apart, side-by-side relation on the footboard.

According to an aspect of the present disclosure, a hospital bed may comprise a physiologic monitor sensing at least one physiologic parameter of a patient supported by the frame and a pneumatic therapy device operable to delivery therapy to the patient. The hospital bed may further comprise a plurality of graphical displays. A first graphical display of the plurality of graphical displays may be included as part of a headboard and a second graphical display of the plurality of graphical displays may be included as part of the footboard. One of first and second graphical displays may show information pertaining to one of the physiologic monitor and the pneumatic therapy device. The other of the first and second graphical displays may show information pertaining to the other of the physiologic monitor and the pneumatic therapy device.

In some embodiments, the first graphical display shows data pertaining to the physiologic monitor and the second graphical display shows information pertaining to the pneumatic therapy device. The pneumatic therapy device may comprise a respiratory therapy garment worn by a patient for high frequency chest wall oscillation therapy. Alternatively or additionally, the pneumatic therapy device may comprise a sequential compression therapy sleeve worn by a patient for prevention of deep vein thrombosis. The hospital bed may have a third graphical display included as part of a first siderail of the plurality of siderails. The third graphical display may show information pertaining to at least one of the physiologic monitor and the pneumatic therapy device.

According to another aspect of the present disclosure, a hospital bed may comprise a frame and hospital bed electronics carried by the frame. The hospital bed electronics may control each of the following: movement of portions of the frame to reposition a patient, operation of an IV pump, operation of a vital signs monitor, and operation of a therapy device.

The hospital bed may have at least one barrier coupled to the frame as well as having at least one graphical display that is included as part of the barrier. The at least one graphical display may display information pertaining to operation of the IV pump, information pertaining to operation of the vital signs monitor, and information pertaining to operation of the therapy device.

The hospital bed may have user inputs that are carried by the barrier and that are usable to command the hospital bed electronics regarding control of the operation of the IV pump, the vital signs monitor, and the therapy device. The therapy device may comprise a respiratory therapy garment worn by a patient for high frequency chest wall oscillation therapy or a sequential compression therapy sleeve worn by a patient for prevention of deep vein thrombosis.

The hospital bed electronics may communicate via wireless signals with at least one computer device that is spaced from the hospital bed. In some embodiments, the hospital bed electronics may include a patient audio port to which a patient may attach a personal audio player. In some instances, the hospital bed electronics may be communicatively coupled via a hospital network to a medical records system and further comprising a keyboard coupled to the hospital bed electronics for entering patient vital signs information into a patient medical record via the hospital bed electronics.

According to one illustrative embodiment, a patient support system is provided comprising a deck, a base, a patient sensor, and an edge board along the deck. The deck is configured to support a patient, and the base supports the deck. The patient sensor is configured to monitor a vital sign of the patient. The edge board is positioned along an edge of the deck and supported by the base. The board includes a user interface configured to provide an indication of the status of the vital sign. The board may comprise an endboard or a siderail, for example, and may include other user functions for control of the deck.

According to another embodiment, a patient support system, comprising a deck configured to support a patient, a base supporting the deck, and a patient sensor configured to monitor a vital sign of the patient. The system further includes a component sensor configured to monitor the status of a component on the patient support, such as an actuator for example. An electronic circuit provided on the patient support system is configured to receive signals from the patient sensor and the component sensor. The system further includes a siderail board which is positioned adjacent a side edge of the deck, and an endboard which is positioned adjacent an end edge of the deck. In addition, the system includes a user interface system which is supported by the endboard and/or siderail. The user interface system is configured to receive signals from the electronic circuit to indicate the status of the patient vital sign and the component sensor.

In accordance with another embodiment, a patient support system is provided, which comprises a deck configured to support a patient, a base supporting the deck, a power cord configured to provide electrical power to the patient support system, and a patient monitor supported by the base and configured to monitor a vital sign of the patient. The system also includes a component sensor supported by the base and configured to monitor the status of a component on the patient support, and a pump supported by the base and configured to deliver therapy and/or medication to the patient. An actuator is supported by the base and configured to move at least a portion of the deck relative to the base. The system further includes a user interface system supported by the base. The user interface system is configured to receive signals from the component sensor and the patient monitor and to allow control of the actuator and the pump. In addition, the patient support system includes a power circuit configured to receive the electrical power from the cord and provide power to the actuator, the pump, the patient monitor, and the user interface system.

In another embodiment, a patient support system is provided which comprises a deck configured to support a patient, a base supporting the deck, a power cord configured to provide electrical power to the patient support system, and a patient monitor circuit supported by the base and configured to monitor a vital sign of the patient. The patient support system further includes a component sensor supported by the base and configured to monitor the status of a component of the patient support system, and a pump supported by the base and configured to deliver therapy and/or medication to the patient. In addition, the system includes an actuator supported by the base and configured to move at least a portion of the deck relative to the base, and a user interface system supported by the base. The user interface system is configured to receive signals from the component sensor and the patient monitor and to allow control of the actuator and the pump. The patient support system further includes a microprocessor board supported by the base and configured to control operation of the pump and the actuator and to receive signals from the component sensor and the patient monitor circuit. Additionally, the patient support system of this embodiment includes a communication circuit supported by the base and connected with the microprocessor board. The communication board is configured to communicate signals indicating the status of the component sensor and at least one of the pump and patient monitor circuit to a remote location, such as to nurses station down the hall from the hospital room within which the patient support system is located. The patient support system further includes a power circuit configured to receive the electrical power from the cord and provide power to the actuator, the pump, the patient monitor, the microprocessor board, the communication circuit, and the user interface system.

According to another embodiment, a patient support system is provided comprising a deck configured to support a patient, a base supporting the deck, an actuator configured to move the deck relative to the base, and a pump supported by the base. In addition, the system includes a connector supported by the base and configured to place the pump into fluid communication with an air mattress, and a connector supported by the base and configured to place the pump into fluid communication with at least one of a sequential compression therapy device, a chest wall oscillation device, and a medication pumping device. Furthermore, the system includes a control system supported by the base and configured to control the actuator and the pump. Additionally, the patient support system includes a user interface system supported by the base and configured to modify the control of the control system to control the actuator and the pump, to thereby allow user control of the actuator, the mattress, and at least one of the sequential compression therapy device, the chest wall oscillation device, and the medication pumping device. Accordingly, the user can control the patient support (e.g., bed) functions, the air mattress, and medical equipment through the bed.

In another embodiment, a patient support system is provided comprising a deck configured to support a patient, a base supporting the deck, an actuator configured to move the deck relative to the base, a board such as an endboard configured to locate an edge of the deck, and an audio connector provided on the board and configured to receive a plug from an audio device. In addition, the patient support system includes a speaker supported by the base, and an electronics system supported by the base and configured to control the actuator and to drive the speaker according to the signal from an audio device. Accordingly, audio from devices such as MP3 players, laptops, cell phones, and the like can be played directly through the bed systems. In some embodiments, instead of or in addition to the audio connector, the endboard can include a data connector to connect the patient support system to a health information system or an electronic medical records system.

In yet another embodiment, a patient support system is provided comprising a deck configured to support a patient, a base supporting the deck, an actuator configured to move the deck relative to the base, a board configured to locate an edge of the deck, and a telephone storage recess provided on the board and configured to receive a telephone. In addition, the patient support system includes an electronics system supported by the base and configured to control the actuator and to control the communication of signals to and from a telephone. The electronics may connect wired or wireless to the phone and to a PBX or cellular system to allow the patient to place calls directly from the bed and via the bed system.

According to one embodiment, a patient support system is provided, comprising a deck configured to support a patient, a base supporting the deck, and an actuator configured to move the deck relative to the base. The system further comprises at least one board such as an endboard or footboard or siderail configured along at least one edge of the deck and supported by the base. The board includes at least one user interface configured to control the actuator. The user interface is further configured to control or monitor medical equipment, such as SCT equipment, hear rate monitors, blood pressure monitors, respiratory therapy equipment and the like. The patient support system comprises one or more of an obstacle detection system, a bed exit alarm system, a head of bed angle alarm system, a safety indicator indicating the bed is in a safe condition, a scale system, a powered transport system, and a patient turn assist system.

According to another embodiment, a patient support system is provided comprising a deck configured to support a patient, a base supporting the deck, an actuator configured to move the deck relative to the base. The patient support system further comprises an electronic control system supported by the base and provided at one location along the patient support system, such as at the base, under the deck, in an endboard or the like. The electronic control system is configured to control the actuator and to receive signals from and/or provide signals to at least one of a consumer electronics device, a patient monitoring device connected to the patient, and a patient therapy device attached to the patient. Other electronics can also be provided throughout the patient support system. The patient support system further comprises one or more of an obstacle detection system, a bed exit alarm system, a head of bed angle alarm system, a safety indicator indicating the bed is in a safe condition, a scale system, a powered transport system, and a patient turn assist system.

These and other features, alone or in combination with any other feature(s) (such as those described herein and/or those listed in the claims) may comprise patentable subject matter. Such features and principles of the disclosure will become apparent to those skilled in the art upon consideration of the following detailed description of various examples and embodiments illustrating the best mode of carrying out the features and principles as presently perceived.

BRIEF DESCRIPTION OF THE DRAWINGS

Referring now to the illustrative examples in the drawings, wherein like numerals represent the same or similar elements throughout.

DETAILED DESCRIPTION

In general, a patient support system is provided having an electronic control system and user interface. In one embodiment, the electronic control system and user interface are provided on a hospital bed and can control bed functions, such as articulation of the head, seat, and leg sections of the bed deck. The electronic control system and user interface of the bed are also configured to control and/or monitor the operation of medical equipment, such as heart rate monitors, blood pressure monitors, thermometers, sequential compression therapy devices, blood warmers, IV pumps, chest wall oscillation devices, respiratory therapy devices, blood oxygen monitors, and the like. In addition, in some embodiments, the electronic control system and user interface of the bed are also configured to communicate with patient personal digital devices, such as audio players, computers, and phones. Furthermore, the electronic control system and user interface of the bed in some embodiments are configured for audio and data communication, wired or wirelessly, with remote hospital computers and communication devices. In one embodiment, a pump system is resident on the bed and is controlled by the electronic control system and user interface, for control of a powered air mattress on the bed deck, and for control of one or more pieces of medical equipment that utilize an air pump. The user interface may be provided in one or more of the endboards of the bed (such as the headboard or footboard) and/or on a siderail board of the bed.

Figure 1:
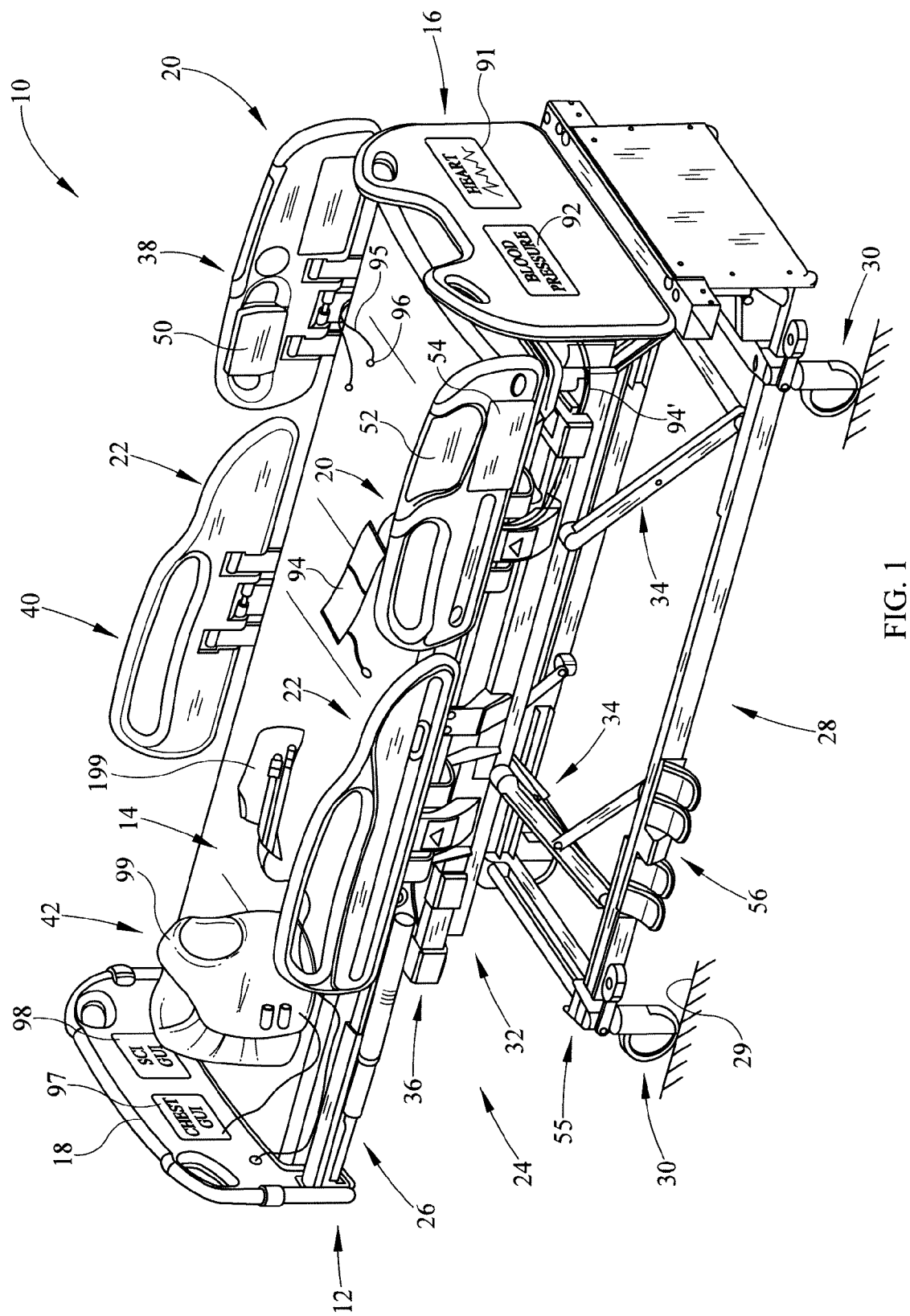
FIG. 1 is a perspective view of a patient support showing a patient support according to one embodiment including one or more principles of the present disclosure.
Figure 2:
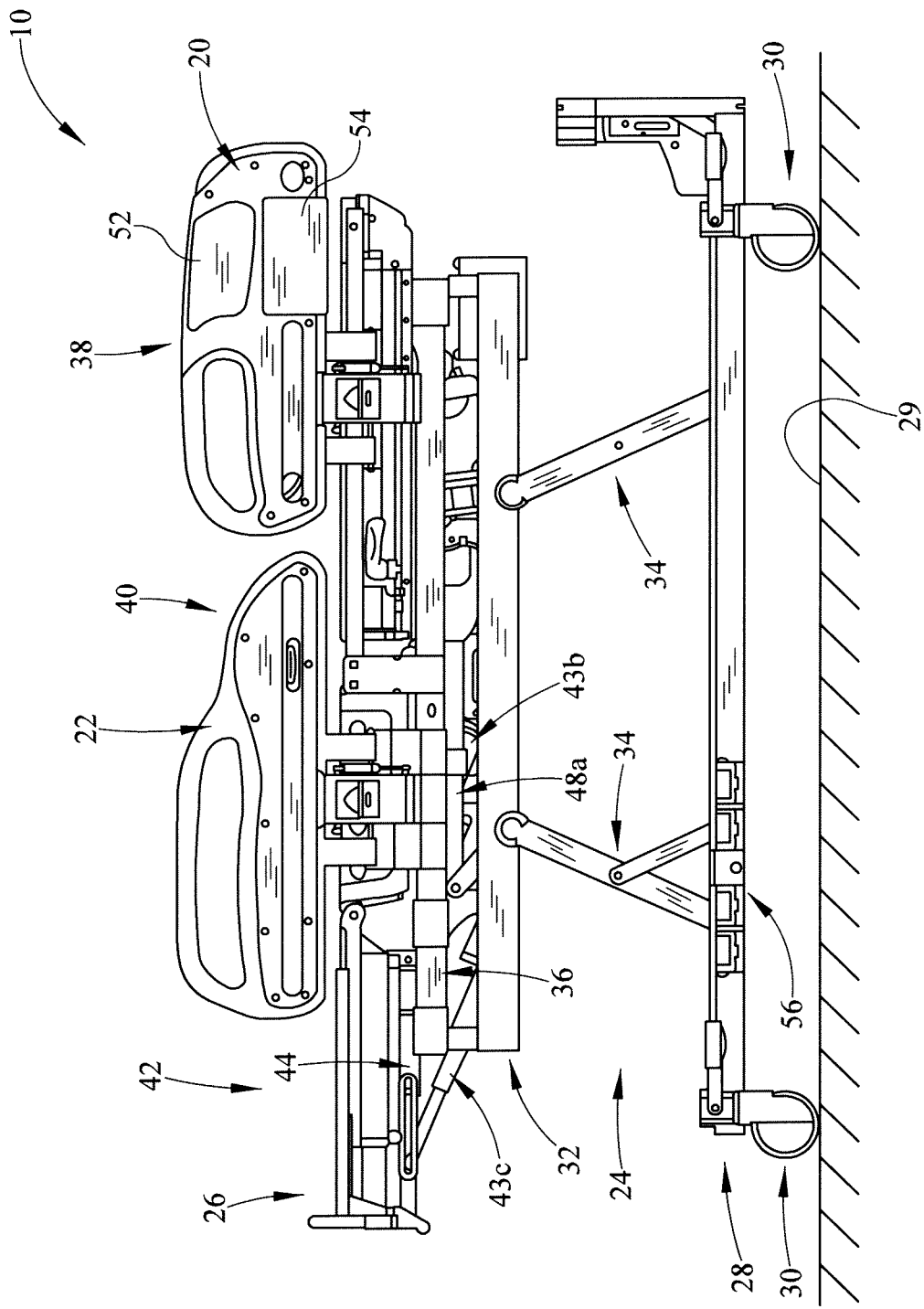
FIG. 2 is a side elevation view of the patient support of FIG. 1, showing the deck support in an upper position and the deck sections in a linear relationship or bed configuration.
Figure 3:
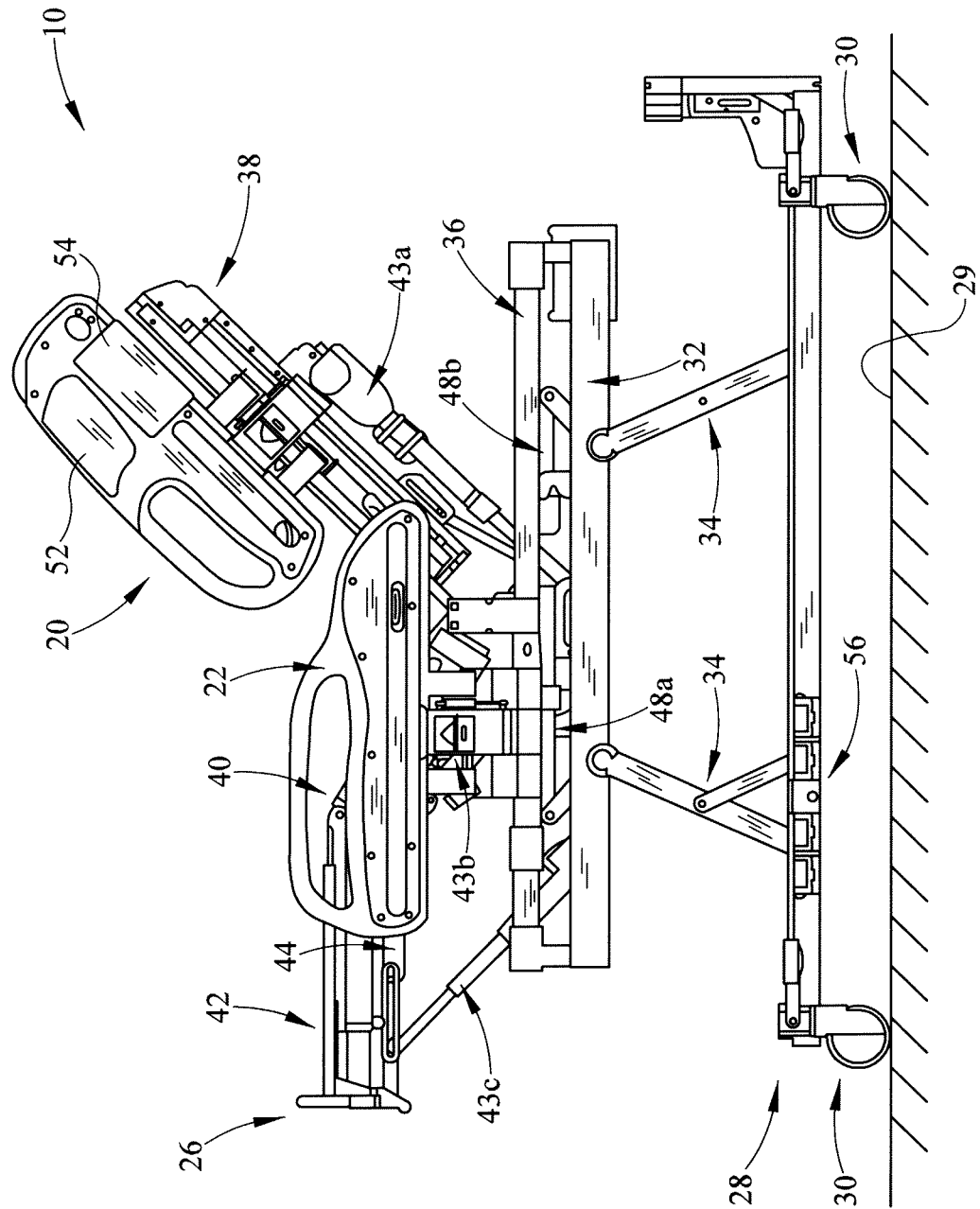
FIG. 3 is a side elevation view of the patient support of FIG. 1, showing the deck support in the upper position of FIG. 2 and a head section of the deck elevated by a head section actuator and a seat section of the deck elevated by a seat section actuator.

A patient support 10 according to an illustrative embodiment of the present disclosure is shown in FIGS. 1-3. Patient support 10 includes a frame 12, a mattress 14 supported by frame 12, a headboard 16, a footboard 18, a pair of head end siderails 20, and a pair of foot end siderails 22. Frame 12 includes a deck support 24 and a deck 26 supporting mattress 14. Deck support 24 includes a base frame 28 supported on the floor 29 by a plurality of caster wheels 30, an intermediate frame 32, first and second pairs of lift arms 34 configured to raise and lower intermediate frame 32 relative to base frame 28, and a weigh frame 36 supported by intermediate frame 32, so as to allow the patient support 10 to be raised and lowered to any position between a high and a low position.

Deck 26 is supported by weigh frame 36 and is configured to articulate between a plurality of positions. More particularly, deck 26 illustratively includes a head section 38 pivotably coupled to weigh frame 32, a seat section 40 pivotably coupled to weigh frame 32, and an adjustable length leg section 42 pivotably coupled to seat section 40. The deck 26 is illustrated in a first configuration in FIGS. 1 and 2, while the deck 26 is illustrated in a second configuration in FIG. 3. In the first configuration of FIGS. 1 and 2, head section 38, seat section 40, and leg section 42 are in a substantially linear or planar relationship. In the second configuration of FIG. 3, head section 38 of deck 26 is elevated by a head section actuator 43a and seat section 40 of deck 26 is elevated by a seat section actuator 43b. A leg section actuator 43c is likewise configured to move leg section 42 relative to seat section 40. An extension actuator 44 is configured to extend and retract the adjustable length leg section 42.

Additional details of illustrative deck support 24 and deck 26 may be found in U.S. Pat. No. 6,658,680, issued Dec. 9, 2003 and U.S. Pat. No. 6,611,979, issued Sep. 2, 2003, both of which are assigned to the assignee of the present application and the disclosures of which are expressly incorporated herein by reference.

Head end siderails 20 are coupled to head section 38 of deck 26 and may be moved relative to mattress 14 between raised and lowered positions. Foot end siderails 22 are coupled to weigh frame 32 and may also be moved relative to mattress 14 between raised and lowered positions.

Figure 4:
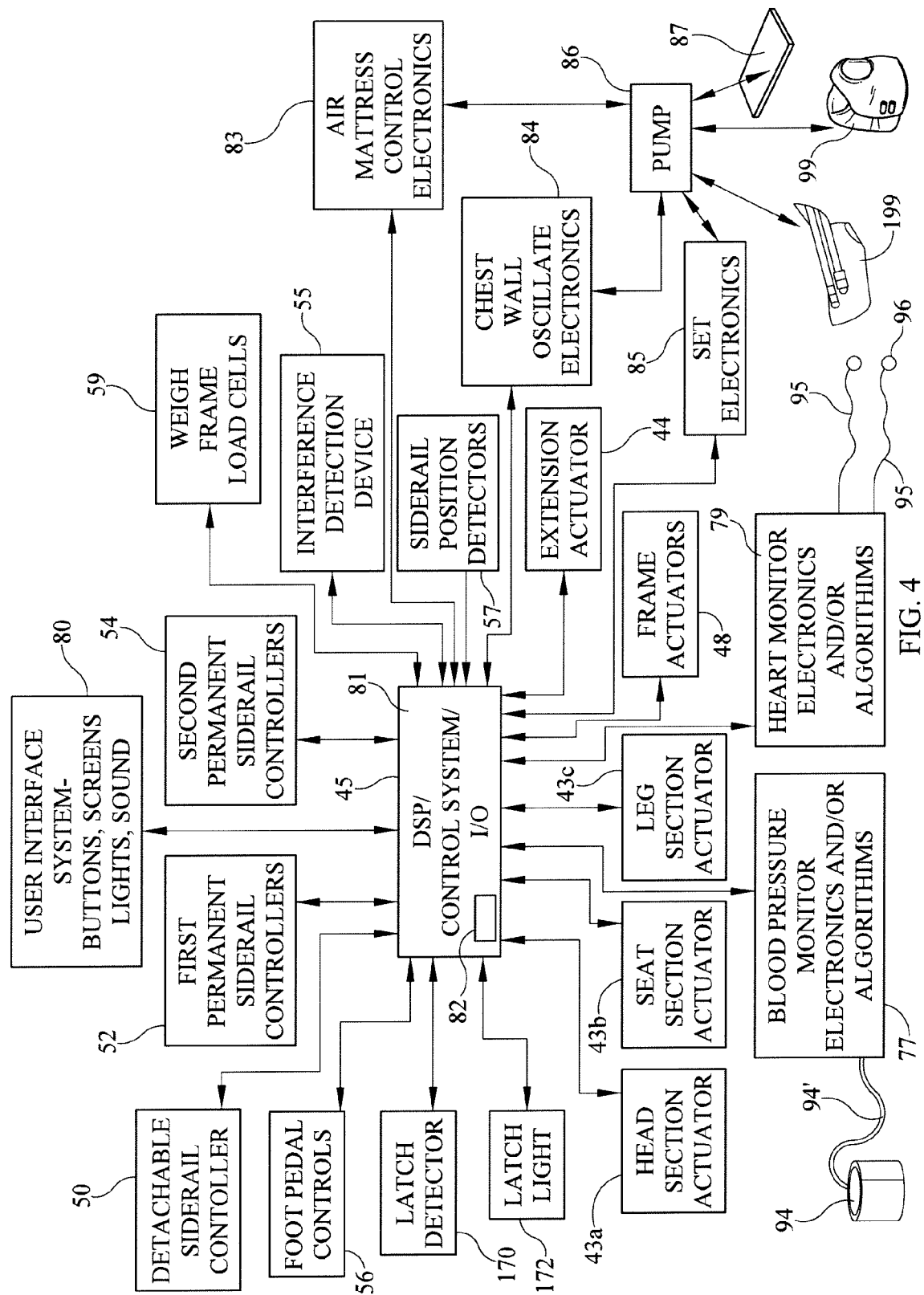
FIG. 4 is a block diagram illustrating communication between the control system and various components of the patient support according to one or more principles of the present disclosure.

Referring now to FIG. 4, a control system 45 provides control of various functions of patient support 10. Control system 45 operates and monitors linear actuator 44 to extend and retract adjustable length leg section 42, and linear actuators 48 to move intermediate frame 32 relative to base frame 28. Control system 45 further operates and monitors linear actuators 43a, 43b and 43c to move head section 38 relative to weigh frame 36, seat section 40 relative to weigh frame 36, and leg section 42 relative to seat section 40, respectively.

Control system 45 includes a plurality of input devices including a detachable siderail controller 50 configured to removably couple to any of head and foot end siderails 20, 22, a first pair of permanent siderail controllers 52 coupled to head end siderails 20, a second pair of permanent siderail controllers 54 pivotably coupled to head end siderails 20, and a pair of foot pedal controls 56 coupled to base frame 28.

Control system 45 also illustratively includes an interference detection device 55 coupled to base frame 28 to detect possible clearance issues between intermediate frame 32 and base frame 28. Control system 45 further illustratively includes a plurality of actuator position detectors or motor sensors (not shown) provided with each of the plurality of actuators 43a, 43b, 43c, 44, 48. A plurality of load cells 59 are provided between weigh frame 36 and intermediate frame 32 to provide signals that indicate the weight supported by intermediate frame 32. Control system 45 uses these signals to determine the weight of a patient positioned on mattress 14. Additionally, control system 45 illustratively includes a plurality of siderail position detectors or sensor 57 configured to provide signals indicative of the vertical position of siderails 20, 22.

As previously described and as shown in FIG. 1, deck support 24 includes a base frame 28 supported on the floor 29 by a plurality of caster wheels or caster devices 30, an intermediate frame 32, first and second pairs of lift arms 34 configured to raise and lower intermediate frame 32 relative to base frame 28, and a weigh frame 36 supported by intermediate frame 32. Linear actuators 48a and 48b, shown in FIG. 3, provide power to actuate lift arms 34 and in turn to raise and lower intermediate frame 32 relative to base frame 28.

Control panel 698 includes a series of buttons 710 for controlling the various functions of hospital bed 10. Deck 26 includes head, seat, thigh and foot portions or sections that can be tilted relative to intermediate frame 52 and several mechanisms configured to adjust the angular position of these deck sections. As will be described in greater detail below, foot section of deck 26 is extendable, seat section of deck 26 can be tilted relative to intermediate frame 52, head section of deck 26 can be tilted relative to intermediate frame 52.

As shown best in FIGS. 1 and 4, the bed 10 is configured to connect with, control, and monitor a wide variety of devices and equipment. In this example, the endboard 16 is fitted with a pair of displays 91 and 92 for controlling and/or monitoring the operation of a blood pressure sensor and a heart rate sensor, which may be connected to the patient. In this example, the electrical and/or air lines 94' for the blood pressure monitor 94 are managed by attachments (clips, conduits, notches and the like) on the bed frame 36 and/or 55 and connect to an electronic control system (e.g., FIG. 4) resident on the bed (e.g., supported by the base frame 28 by housing the system in or on the frame 32, the endboard 18 and/or the endboard 16). The same is true for the heart rate monitor and its associated lines 95 which connect the sensors/electrodes 96 back to the heart rate monitoring electronics which are resident in the bed's electronic system that are supported by the base frame 28. (Supported as used herein is not limiting and encompasses both indirect and direct support.) Accordingly, the electronics which control the heart rate and blood pressure monitoring are resident on the bed and part of the bed's overall electronic control system. These monitoring tasks and/or the control tasks of the bed can be accomplished using one or more microprocessors resident in the bed's electronic system.

As also shown in FIG. 1, provided in the footboard 18 are GUI's 97 and 98 which can allow for control and/or monitoring of additional devices via the bed's resident electronic system. Here, GUI 98 controls and monitors a sequential compression therapy (SCT) electronics (e.g., processor, circuit or software) that provides SCT therapy to a sleeve 199, to treat deep vein thrombosis (DVT). Additionally, GUI 97 provides control and/or monitoring of a portion of the electronics in the bed that controls respiratory/chest therapy, such as via a respiratory therapy garment 99. Such therapy can comprise high frequency chest wall oscillation for example. Again, the software and/or hardware that control the respiratory therapy and the SCT therapy are part of the bed's electronic control system and can also control other bed functions.

As shown in the block diagram of FIG. 4, the system includes a user interface system 80 resident on the bed and supported by the base frame which controls not only the bed functions, but also the monitoring and therapy equipment functions via a main electronic control system 81. Control system 81 may include digital signal processing functions, input/output control functions, closed loop control functions, and other logic to control these various features of the bed. One or more microprocessors 82 can execute software and/or firmware to provide such control. In this example, in addition to the various bed functions controlled by the bed, control system 81 also controls air mattress control electronics 83 (hardware and/or software) for control of a pump 86 to control bladders in an air mattress 87. Additionally, control system 81 controls chest wall oscillation electronics 84 that control pump 86 to control the respiratory therapy garment 99, such as one worn on the upper body. Moreover, control system 81 controls SCT electronics 85 for control of an SCT garment 199, such as one worn on the foot or leg. In addition, control system 81 also monitors blood pressure electronics 77 that receive signals from and/or provides control of a blood pressure cuff 94 via lines 94'. Additionally, heart rate monitor electronics 79 are resident in the bed's electronic system and controlled by the control system 81 to monitor the patient's heart rate as monitored by electrodes 96 via lines 95.

Figure 6:
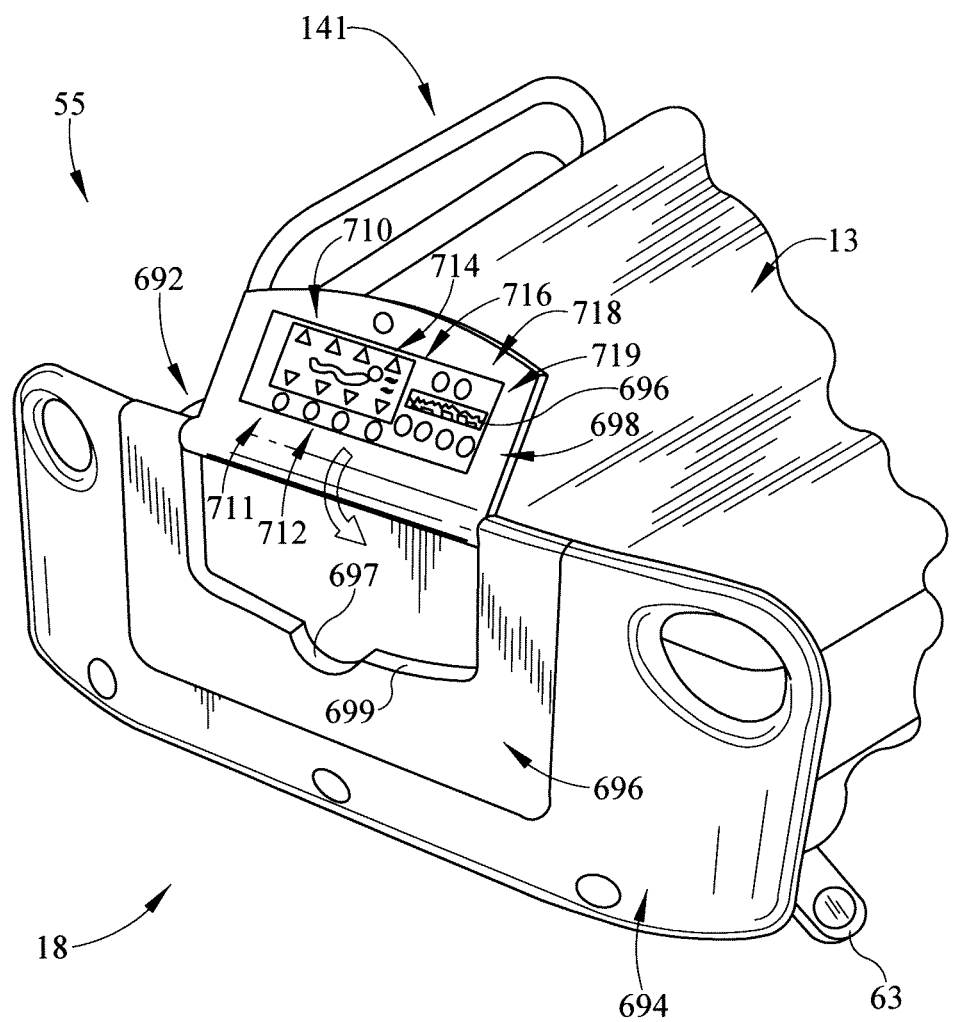
FIG. 6 is a perspective view of a footboard for a patient support, according to another embodiment of the present disclosure.

As shown in FIG. 6, as another alternative, a footboard can be fitted with patient and/or vital signs monitor device controls and/or readouts and used with a bed, such as the bed of FIG. 1. This embodiment includes a modular control unit 692 for controlling the automated features of hospital bed 10. Footboard 18 further includes a base 694 and modular control unit 692 includes a support panel 696 slidably coupled to base 694 and a control panel 698 pivotably coupled to support panel 696. Control panel 698 is rotatable between a use position, as shown in FIG. 6, and a storage position in a recess 699 formed in support panel 696. Support panel 696 is also formed to include a notch 697 in which a caregiver can grab a distal end of control panel 698 to rotate it back to the use position. Series of buttons 710 also includes a third pair of buttons 714 for raising and lowering back section relative to intermediate frame and a fourth pair of buttons 716 for simultaneously raising and lowering seat and back sections. Another set of buttons 718 is provided for controlling the various functions of a mattress on the bed. Series of buttons 710 includes a first pair of buttons 711 for raising and lowering intermediate frame (e.g., 32 of the embodiment of FIG. 1) and a second pair of buttons 712 for raising and lowering seat section (e.g., 40 of the bed of FIG. 1).

Control panel 698 further includes a display 719 for monitoring the status of the various functions of hospital bed. According to an alternative embodiment, the series of buttons also includes a pair of buttons for moving the intermediate frame between the Trendelenburg and reverse Trendelenburg positions, extending and retracting the foot section of the deck, and any other function of the bed. Control panel 698 can also include buttons and a display associated with a bed exit and weighing system of bed. Here, patient vital signs and/or other monitoring information about the patient are displayed on interface 696. This interface 696 may be a display, such as an LCD and/or light indicators, or other device for displaying information to the user.

As shown in FIG. 6, control unit 692 is removable from base 694 to permit replacement of control unit 692 for repairs or upgrading. Multiple configurations of modular control units can be provided at the manufacturing facility. Depending on the specific configuration of the hospital bed, a different control unit can be provided with the respective hospital bed by sliding the respective control unit into standard base 694.

As further shown in FIG. 6, the endboard 18 can include a screen or other display 696 which indicates the status of one or more patient monitors. The monitors may be integrated with the bed, as described in further detail above, or may be plugged into data ports on the bed. The patient monitors may monitor vital signs such as heart rate, respiration rate, temperature, blood pressure, blood oxygen saturation, and other signs regarding the patient. Accordingly, in this embodiment, a single user interface, and circuitry associated therewith, can be utilized for control of the patient support system and for monitoring the patient.

Figure 9:
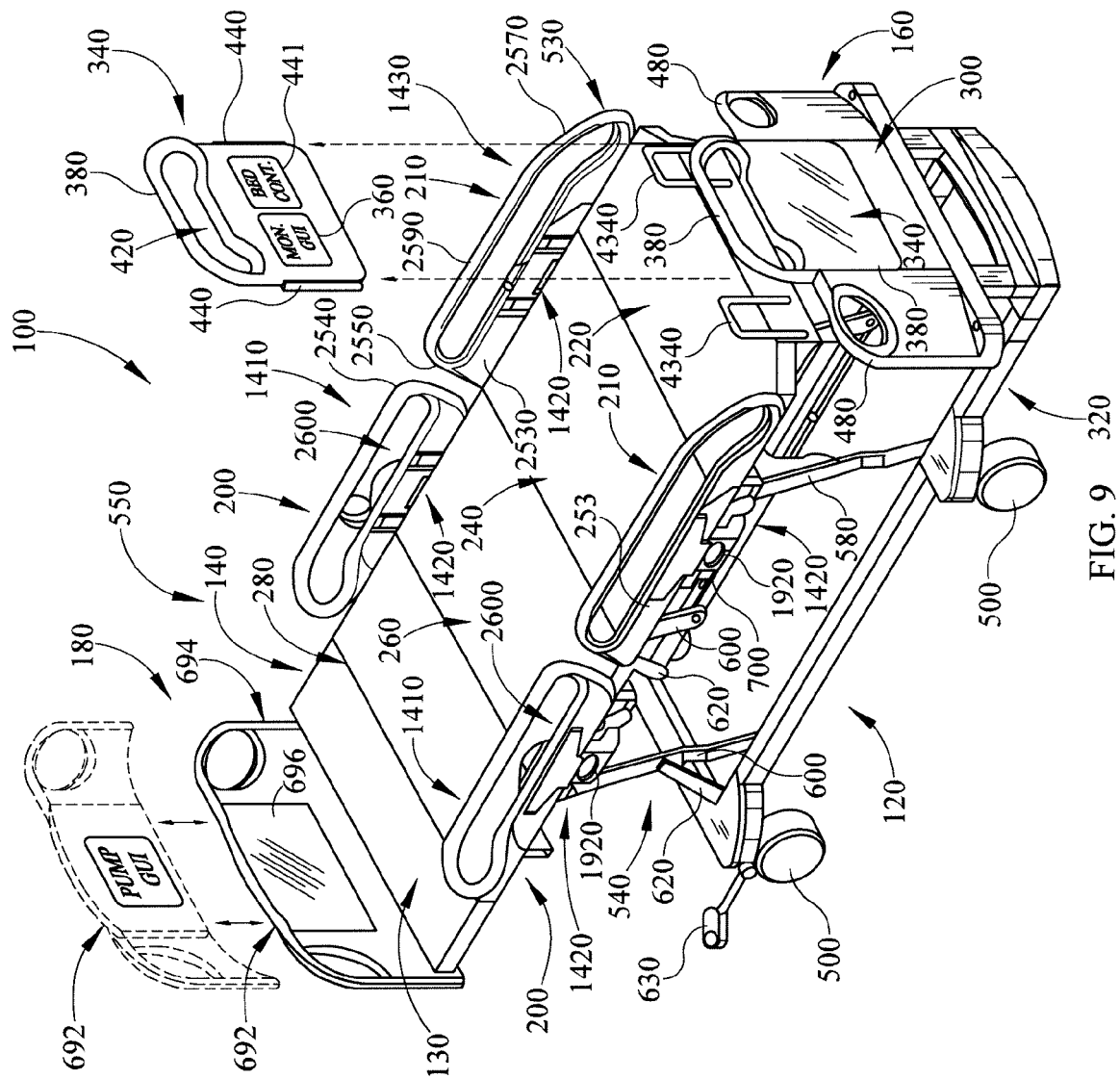
FIG. 9 is a perspective view of another embodiment of a patient support system in the form of a hospital bed, according to one or more principles of the present disclosure.

As shown in FIG. 9, in another embodiment a hospital bed 100 is provided including a base frame 120 positioned on the floor, a deck 140 coupled to frame 120, a mattress 130 positioned on deck 140, a headboard 160 coupled to frame 120, a footboard 180 coupled to deck 140, and a pair of split siderails 200, 210 coupled to frame 120. Frame 120 is configured to raise and lower deck 140 relative to the floor and to move deck 140 to the Trendelenburg position and the reverse Trendelenburg position.

As shown in FIG. 9, headboard or first board 160 includes a curved base 300 coupled to frame 120 and a center panel 340 removably coupled to base 300. Base 300 includes a pair of handles 480 to facilitate pushing hospital bed 100 about a care facility. In this embodiment, center panel 340 can be removed from base 300 to allow for retrofitting of new user interface headboards based on the desired capabilities of the bed. The removability of center panel 340 can also permit access to the patient during such a procedure from a head end of hospital bed 100.

Base 300 may be formed to include a pair of grooves configured to receive tongues 440 of center panel 340 so that center panel 340 is slidably coupled to base 300. As shown in FIG. 9 frame 120 can include a rectangular lower frame member or base frame 320, a plurality of casters 500 coupled to base frame 320 to permit hospital bed 100 to be rolled about a care facility, a rectangular upper frame member or intermediate frame 520, a linkage system 540 coupled to intermediate and base frames 520, 320 to permit relative motion therebetween, and an actuator system 560 providing power to actuate linkage system 540 and move upper member 520 relative to base frame 320. Linkage system 54 includes a pair of head links 580 pivotably coupled to a head end 530 of intermediate frame 520 and slidably coupled to base frame 320, a pair of foot links 600 pivotably coupled to a foot end 550 of intermediate frame 52 and slidably coupled to base frame 320, and a pair of guide links 620 pivotably coupled to respective foot links 600 and pivotably coupled to base frame 320 at a fixed pivot point.

In this embodiment, the module 692 which is movable into and out of engagement with the footboard 694 comprises a display, such as a graphical user interface LCD or the like, which monitors the operation of and/or allows control of a pump. The pump may be an IV pump, an air pump for the mattress 260, an air pump for a sequential compression therapy device (for DVT), an air pump for a respiratory therapy (such as high frequency chest wall oscillation therapy), or other medical pump. In addition, in this embodiment, the headboard panel 340 includes a display 360 (e.g., lights, screen, and/or GUI) for controlling the operation of and/or monitoring a patient vital signs monitor. In addition, the board 340 includes a display 441 for monitoring and/or controlling the bed functions, such as the hi-lo function, the articulation functions, and the Trendelenburg functions.

Figure 5:
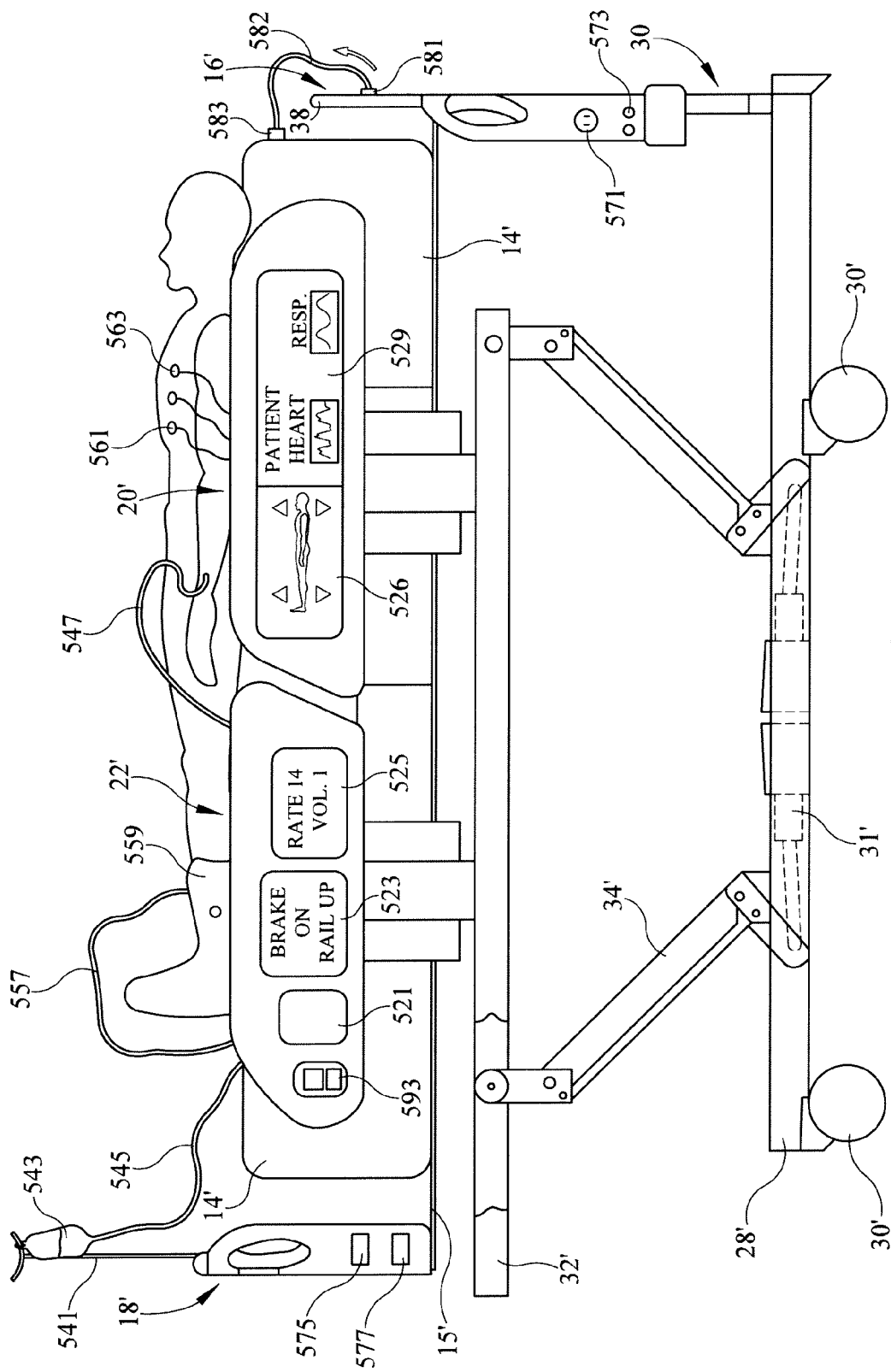
FIG. 5 is a side view of a patient support system according to another embodiment, in accordance with one or more principles of the present disclosure.

Another embodiment of a patient support apparatus having a multifunctional unified control and user interface system is shown in FIG. 5. Here the base frame 28' support an intermediate frame 32' and a deck 15' upon which rests a mattress 14'. Actuators 31' move links 34' to permit movement of the frame 32' relative the base 28'. Casters 30' allow for movement of the bed. Various boards are provided along edges of the bed to locate the edges of the bed and assist the patient and caregiver. In particular, endboards in the form of headboard 16' and footboard 18' are provided at the short sides of the bed and various side boards, also known as siderails 20' and 22' are provided at the long sides of the bed. Each of these boards in this example provides controls or user interface capabilities for hospital equipment and/or patient devices. For example, siderail 22' includes a GUI 521 for controlling and/or monitoring the status of a pump for use in treating DVT, a GUI 523 for use in controlling and/or monitoring the actuators on the bed, and a GUI 525 for controlling and/or monitoring the status of an intravenous (IV) pump. The IV pump can be located on the bed and supported by the base 28' and used to deliver fluid from IV bag 543, which is retained on IV pole 541, through line 545, through the pump and ultimately through line 547 to the patient vein. The lines 545 and 547 can be retained to the deck 15, the frame 32', and/or the base 28', via suitable connectors, conduits, clips, and/or retainers. Like the IV pump and its associated electronics, the DVT pump and its associated electronics can likewise be provided on and built into the bed infrastructure. The DVT pump can thus provide SCT therapy through line 557 to DVT sleeve 559 on the patient's lower extremity. Additionally, siderail 20' includes a GUI 526 for controlling the bed actuators, and a monitor GUI 529 for controlling and/or monitoring the status of patient vital sign monitors. The monitor GUI 529 receives its signal from sensors 561 and 563 that connect to the patient and which contain cords or lines that can be run along or contained within the frame 32', deck 15' and/or base 28'. The electronics that run the various pumps and monitors can be built into the bed electronics system and unified or integrated therewith.

The headboard 16' of the bed of FIG. 5 includes an AC power outlet 571 for providing AC electrical power to external devices through the bed's infrastructure, as well as an audiovisual connector 573 for allowing an AV component to be hooked to the bed and communicate through the bed's electronic system. For example, an MP3 player or laptop could be hooked up to connector 573 and can play music through the bed's speakers (not shown). In this example, headboard 16' also includes a connector 581 to provide air to the air mattress 14' via air line 582 which connects to an air port 583 on the mattress. The pump that provides the air can be the same pump as the pump that provides the SCT therapy to the sleeve 559, or can be a separate pump, both of which are mounted to the base 28', frame 32', endboards 16'/18', and/or deck 15'. Footboard 18' likewise includes ports for hooking to external devices. In this example, a USB (universal serial bus) port 575 is provided on footboard 18' to allow devices to be powered from and/or communicate with the bed electronics system, and a LAN (local area network) port 577 is provided to allow devices to access a network and/or the Internet from the bed electronics.

A wireless phone 593 is mounted to the siderail 22', such as via a mounting port or station or via a connector or other attachment. The wireless phone 593 can wirelessly communicate with electronics in the bed to allow the phone to be used for calls within the hospital or external calls to the public.

Figure 7:
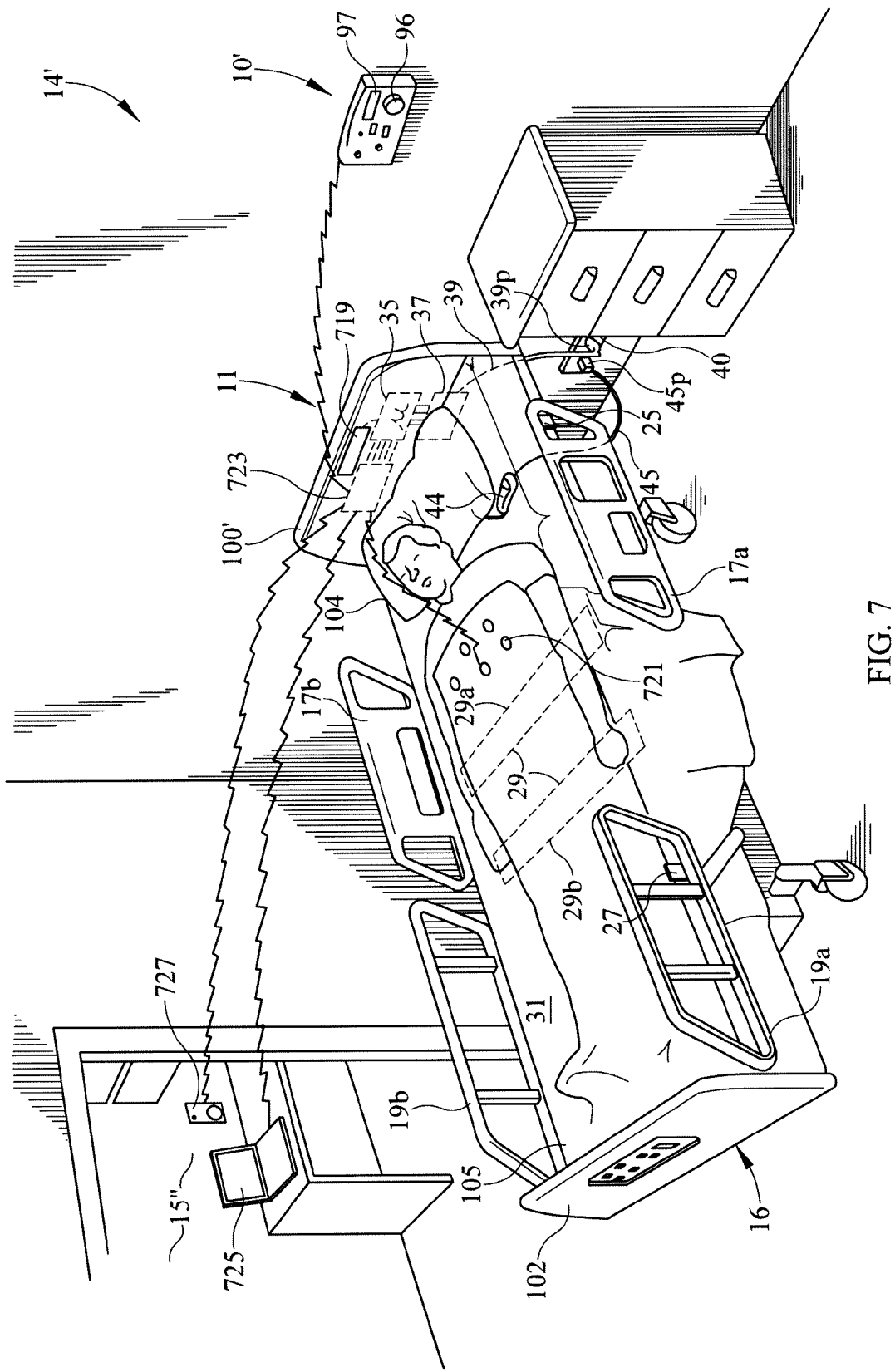
FIG. 7 is a perspective view of another embodiment of a patient support system and surrounding hospital infrastructure, in accordance with one or more principles of the present disclosure.

Another embodiment is shown in FIG. 7. This embodiment includes a bed status system 11, which is integrated with a patient/nurse call system 10' in accordance with a contemplated embodiment of the present disclosure. While bed status system 11 provides bed status information, the patient/nurse communication system 10' organizes, stores, maintains and facilitates retrieval of bed status information, along with the various non-bed calls placed in a hospital wing or ward, thereby optimizing communication capabilities among nurses and patients 12. More specifically, FIG. 7 shows a patient room 14' accessible from a hall 15" of the hospital wing, and a patient bed 16 located in the room 14'. Patient bed 16 is equipped with a variety of mechanical and electrical systems to assist hospital personnel in patient care. The state or condition of each of these systems is detected by circuitry included on bed 16. For example, patient bed 16 includes headrails 17a, 17b and footrails 19a,19b for assisting a patient within the bed. The rails have an up or latched position, as indicated, by headrail 17b, and a down or unlatched position as indicated by headrail 17a. Each headrail 17a, 17b or footrail 19a, 19b of patient bed 16 is equipped with a latch sensor, such as headrail latch sensor 25 and footrail latch sensor 27 to detect whether the respective rails are in the latched or unlatched position. Furthermore, bed 16 is equipped with a patient exit detection system which includes pressure sensitive sensor strips 29 to detect whether the patient 12 has exited the bed or is still in the bed. The patient exit detection system may be armed or disarmed and a sensor (not shown in FIG. 1) indicates whether the system is armed. Other bed system conditions are also detected on bed 16 by various sensor systems. For example, in one embodiment contemplated by this disclosure, bed 16 is equipped with a sensor to indicate whether the bed break is set, a sensor to indicate whether the bed is at its lowest position, and a sensor to indicate whether the mattress 31 is in a particular firmness mode to enhance the comfort of the patient. Furthermore, other various features and functions of the bed might be monitored in accordance with the principles of the present disclosure. The various sensed bed conditions are associated with sensor signals, and the signals are presented via hard wire connections 33 to a bed electronics and interface board 35. Interface board 35 is connected through a junction box 37 to a serial cable 39 and plug 39p which, in turn, connects to a wall interface unit 40, which couples the bed status information to a patient/nurse communication system 10'. As part of the patient/nurse communication system 10' utilized with this embodiment, a patient station 41 is mounted to a head wall of the patient room 14' as shown in FIG. 7. The patient station 41 is connected by a hardwire connector 43 to wall interface unit 40, with connector 43 located behind the headwall of the room 14'. A pillow unit 44, on bed 16, connects via cable 45 to a bed outlet or plug 45p of the wall interface unit 40. Additionally, cable 39 plugs into a bed outlet or plug 39p of the interface unit 40, while a second end of the cable 39 is electrically coupled to bed interface board 35 through junction box 37.

Like the embodiments described above, the bed of FIG. 7 can include one or more side or end boards which display or control other medical devices. Here, a user interface 719 is mounted in the headboard 100' to allow for vital signs of the patient to be displayed. Such vital signs can come from wireless electrodes 721 placed on the patient. A communication board 723 in the bed electronics receives signals from the electrodes 721 as well as from other devices. For example, the communication board 723 can wirelessly communicate bed and/or patient data to a remote computer 725 and/or a nurse call station 727 which are external to the hospital room 14'. The electronics board 35 can include one or more microprocessors that controls and/or communicates with the bed components, the bed sensors (such as 25/27), the monitor/sensors 721, the communication board 723 and the headboard GUI 719.

Figure 8:
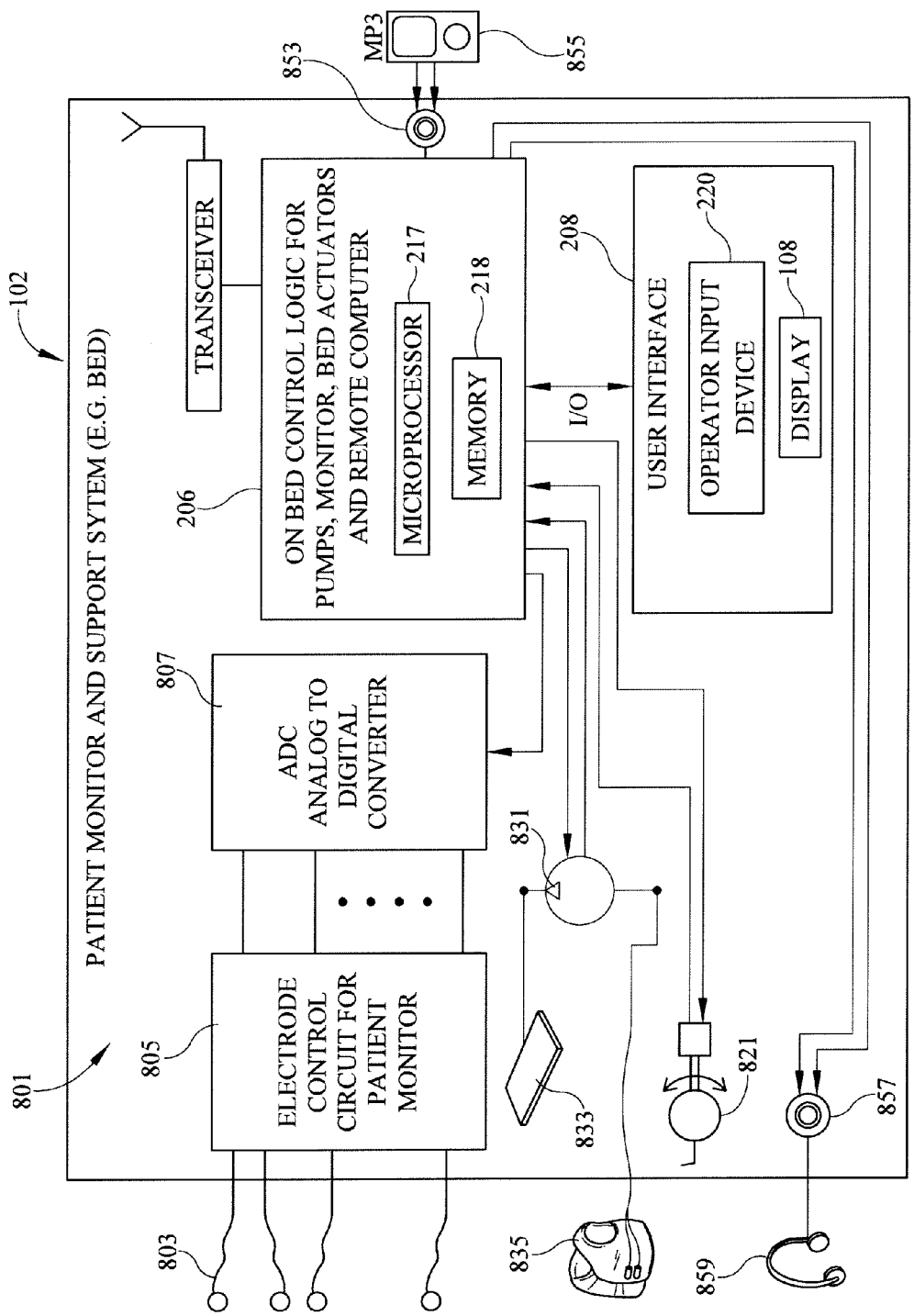
FIG. 8 is a block diagram of yet another embodiment of a patient support system, in accordance with one or more principles of the present disclosure.

Another embodiment of a electronic control system for a patient support having adjustable mechanical components, patient therapy, and patient monitoring system is shown in FIG. 8. In this example, the control system 801 is confined within a patient support (e.g., a bed, stretcher, or wheelchair). The system 801 includes patient sensors 802 that provide patient monitoring signals to a lead/electrode control circuit 805 (which controls the signals provided to and from the electrodes). The output of the control circuit 805 is provided to an analog to digital converter 807 which provides signals representing the vital signs to a main control logic board 206 for the patient support 102. This board 206 may include one or more microprocessors 217 which executes algorithms in the form of software or firmware stored in memory 218. Additionally, the system 801 controls various components of the patient support via at least one motor 821. Control signals to control the motor provided from the control board 206, and monitoring signals regarding the status of the motor (or the mechanical parts it controls) are fed back to the control board 206. Additionally, a pump 831 is provided as part of the patient support system 102. The pump 831 provides air to a mattress 833 and to a respiratory therapy garment 835. The pump is controlled and monitored by the control board 206. The user operates the pump 831 and motors 821, and views the status (and/or history) of these components (as well as the patient vital signs from the sensors 803) via a user interface 208. The user interface 208 can include operator input devices 220 and one or more displays 108 and is in communication with the control board 208 to communicate control signals and display signals therebetween. Additionally, the patient support system 102 includes an AV input 853 to provide audio and/or video signals from an external consumer electronics device, such as an MP3 player 855. Moreover, the patient support system 102 includes an AV output to drive a speaker or headphone system 859. The user interface can be used to control these connections and these devices 859/855. The user interface may also allow for connection to the Internet or to a list of entertainment choices (television shows, songs, etc.), and the entertainment can be delivered via the port 857 to the output device 859. The patient support 102 may include any one or more of the features described above with respect to the other embodiments.

Figure 10:
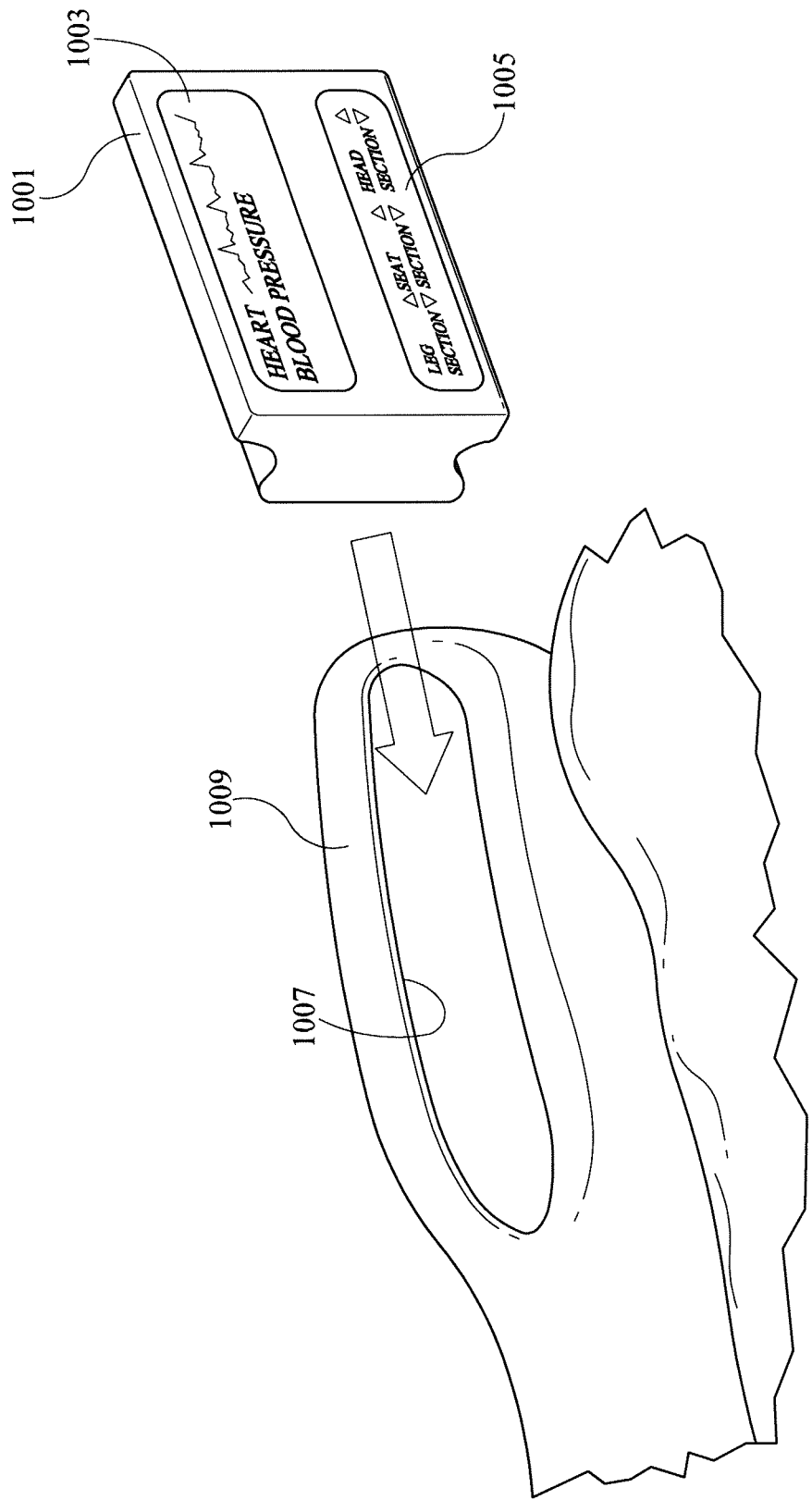
FIG. 10 is a side perspective view of a sideboard or siderail and associated user interface, according to one or more principles of the present disclosure.

FIG. 10 illustrates the shape of a removable GUI device that could be placed within an opening in the board of the patient support system to allow the user to control features of the patient support, as well as to monitor the patient. Here, the user interface device includes a housing 1001 that includes a display 1003 for monitoring patient vital signs, as well as user interface buttons 1005 for controlling movements of the patient support (e.g., the leg, seat and head sections of the deck). The housing 1001 can have a portion that fits into opening 1007 in the sideboard/siderail 1009, such as via interference/snap fit or via attachments. The patient support and siderail 1009 can operate and include components such as those described above.

Figure 11:
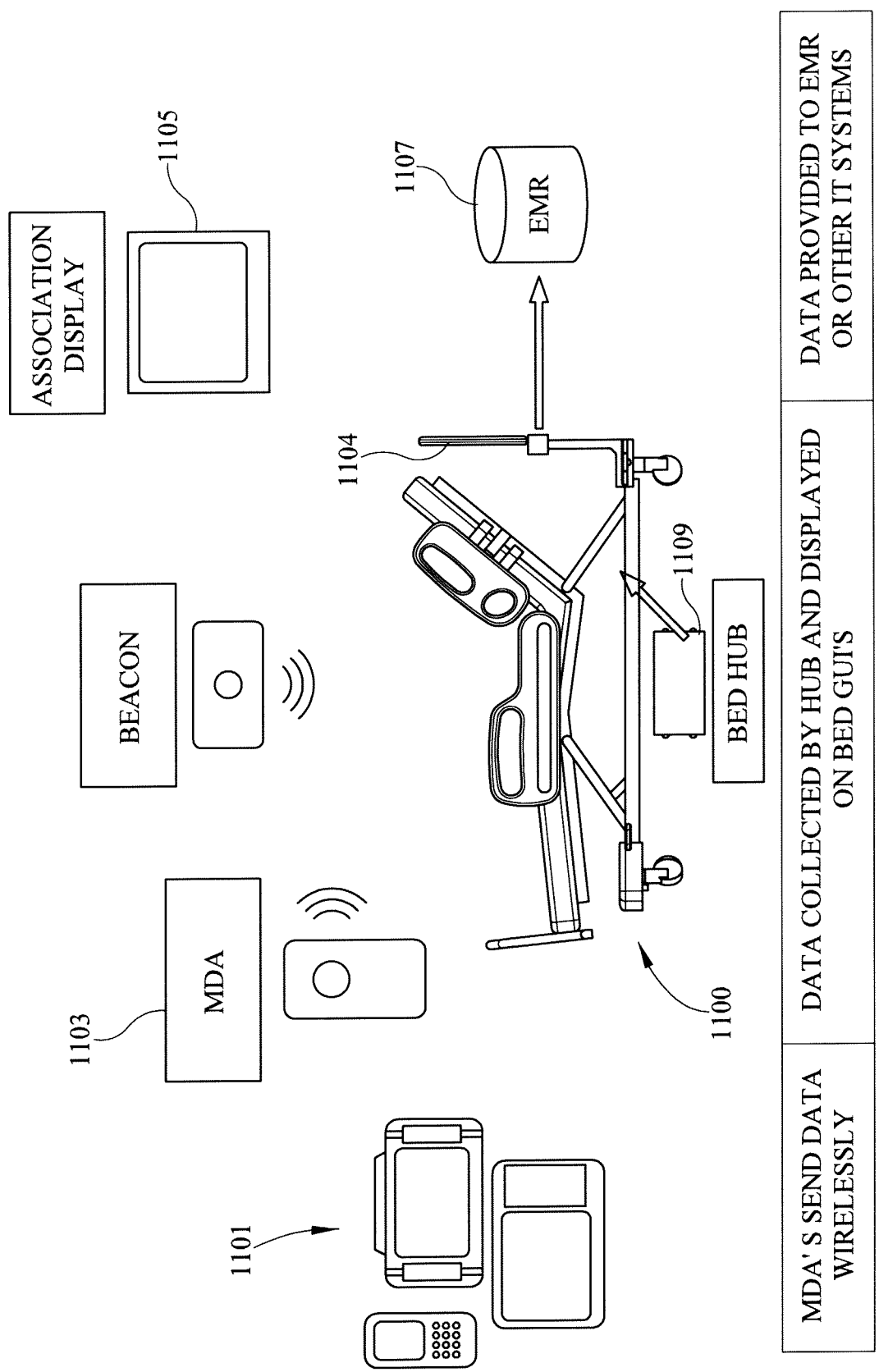
FIG. 11 is a schematic view of a patient support system according to another embodiment having one or more principles of the present disclosure.

FIG. 11 is an embodiment of a patient support system 1100 that is adapted to receive data/vital signs/patient status wirelessly from a variety of medical monitoring devices 1101 via a communication device 1103. A communication device 1109 on the patient support system 1100 receives and aggregates and processes the signals from the devices 1101. A user interface 1105 on the headboard 1104 then displays signals from the monitoring devices 1101. Such data can then be passed along wired or wirelessly to an electronic medical records system (EMR) 1107. The patient support system 1100 can include one or more of the features and components described above with respect to other embodiments.

Figure 12:
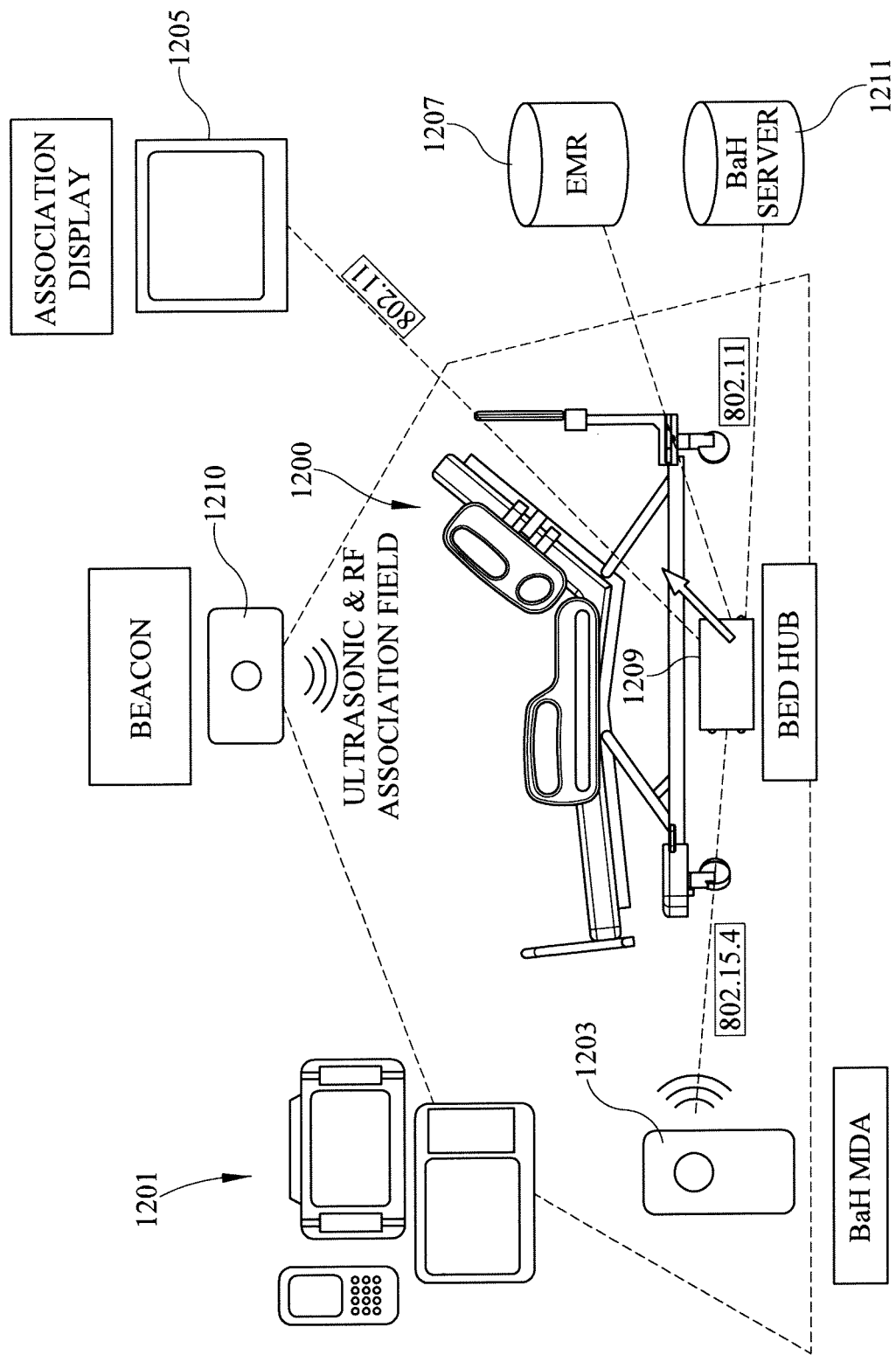
FIG. 12 is a schematic view of another embodiment of a patient support system having one or more principles of the present disclosure.

FIG. 12 illustrates another embodiment. Here, a communication device 1203 on each of the medical devices 1201 communicates wirelessly with a communication device 1209 on the patient support 1200 via IEEE802.15.4 protocol. The location of the patient support 1200 is determined from ultrasonic and RF beacons 1210, such as via location technology. The medical device data is then transmitted to a display 1205, an EMR 1207, and other computers 1211 via wireless IEEE802.11 protocol. The device 1209 can be located on the patient support 1200, as can the display 1205. A display on the headboard or siderail of the support 1200 can display the data from the devices 1201. The patient support system 1200 can include one or more of the features and components described above with respect to other embodiments.

Figure 13:
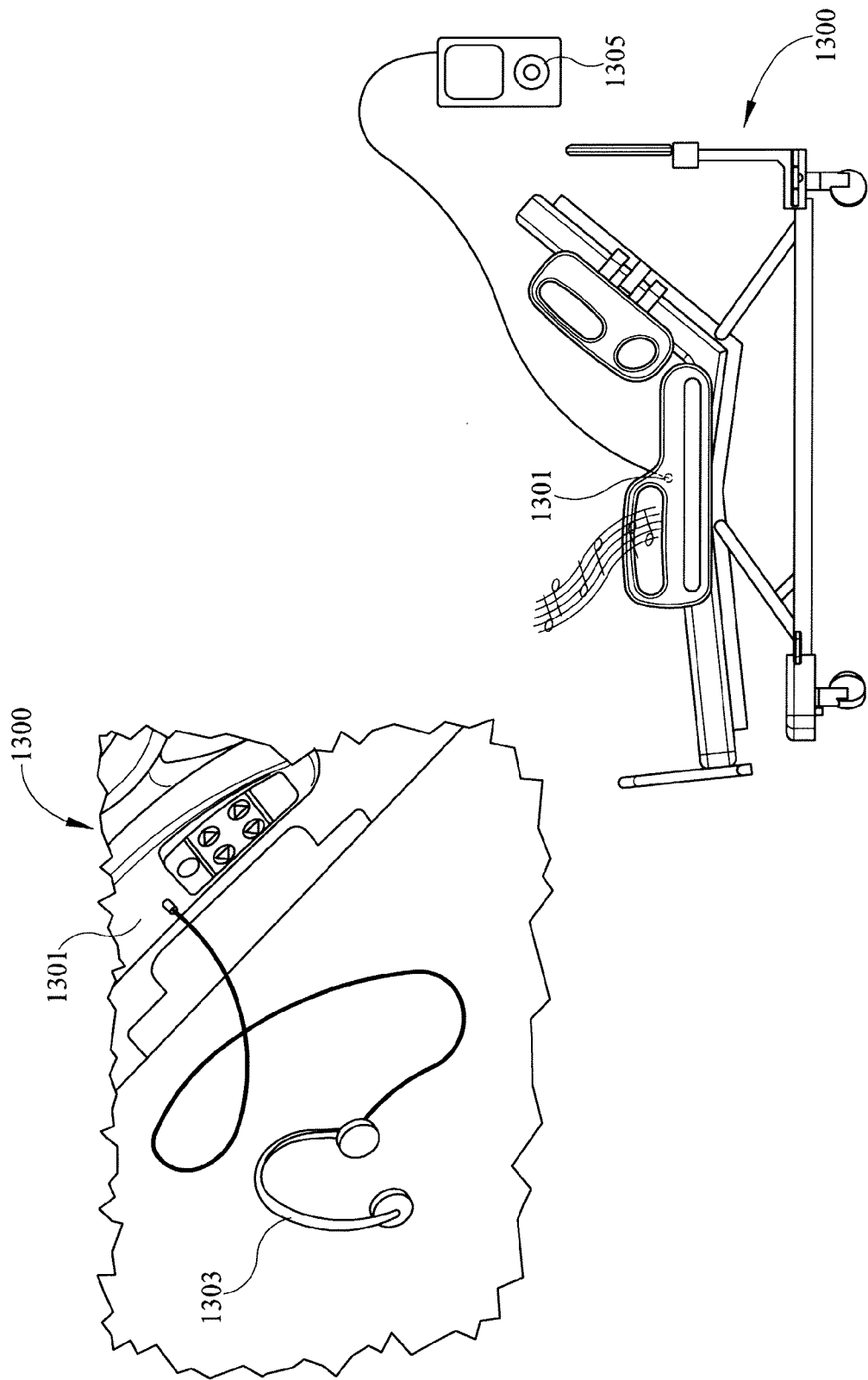
FIG. 13 is a perspective view of a patient support system and of the siderail thereof, according to another embodiment having one or more principles of the present disclosure.

FIG. 13 illustrates another example where the patient support system 1300 (in this example the siderail 1301) includes one or more device ports to plug in headphones or an MP3 or digital audio music player 1305, such as described above. The patient support system 1300 can include one or more of the features and components described above with respect to other embodiments.

Figure 14:
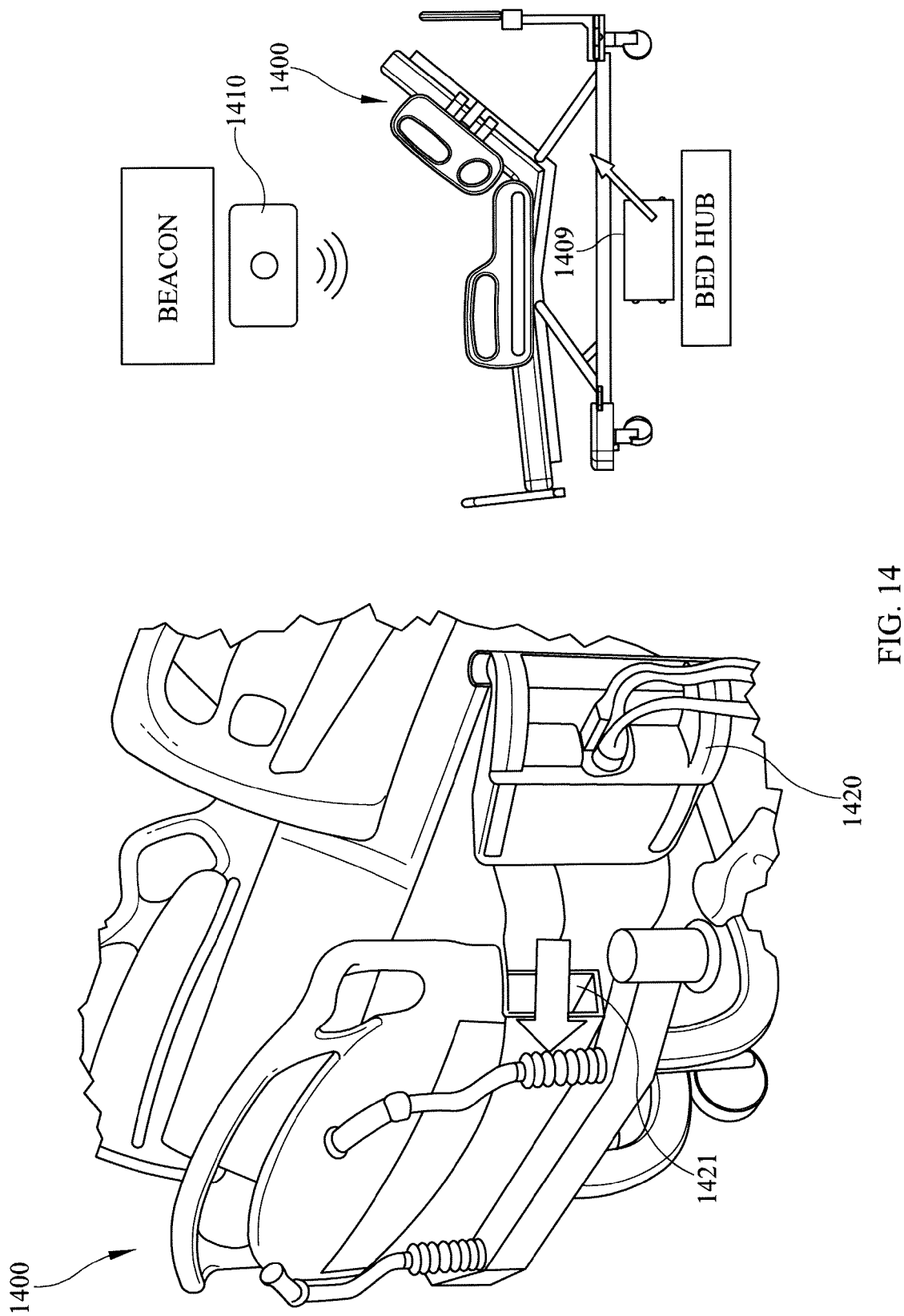
FIG. 14 is a side view of a patient support system and a perspective view of the endboard of a patient support system, according to another embodiment having one or more principles of the present disclosure.

FIG. 14 is another embodiment, similar to that of FIGS. 11 and 12. However, in this example, a data connector or docking port 1420 extends from a hospital room headwall or other wall within the hospital room. This port 1420 then interfaces with the patient support 1400 via a corresponding data receptacle 1421 on the endboard of the bed, allowing for data transfer whenever the bed is hooked to the port 1420 on the wall. Accordingly, the endboard of the patient support system transfers data regarding the bed or equipment and devices controlled by or monitored by the bed, wired or wirelessly. Such data can then be transmitted to remote locations, such as computers or nurses stations, having health information systems and/or Electronic Medical Records, for collection, storage, billing, reporting, and/or analysis. The patient support system 1400 can include one or more of the features and components described above with respect to other embodiments.

Figure 15:
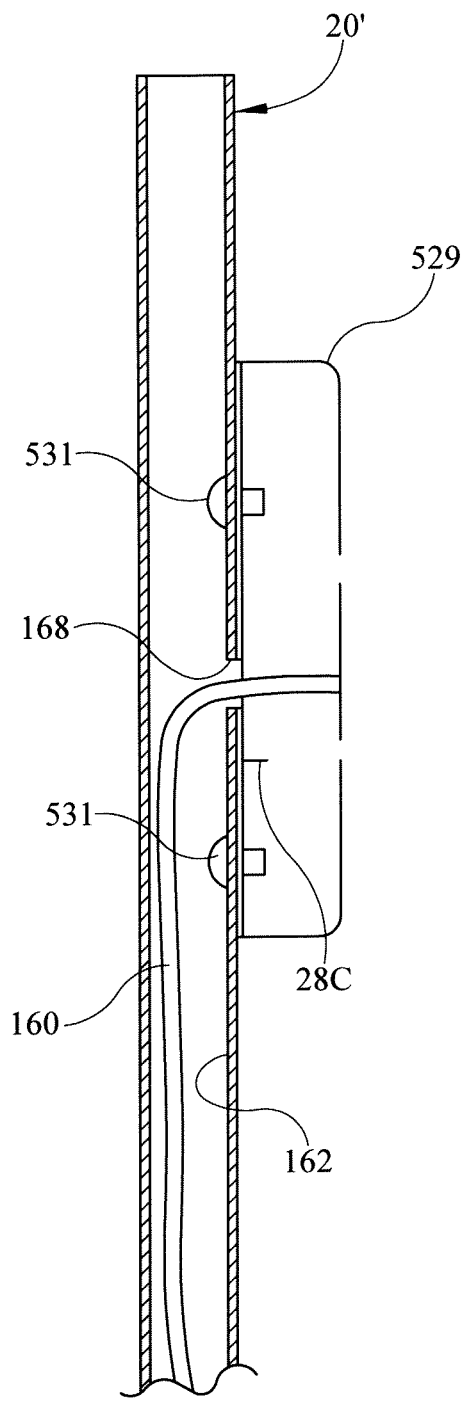
FIG. 15 is a cross-section view of an illustrative embodiment of a siderail 20', such as that of FIG. 5, having an incorporated display 529 for a patient monitor or other medical equipment, according to principles of the present disclosure.

FIG. 15 is a partial cross-section view of an illustrative embodiment of a siderail 20', such as that of FIG. 5, having an incorporated display 529 for a patient monitor or other medical equipment, according to principles of the present disclosure. This Figure illustrates the routing of conductors 160 for equipment display 529. Conductors 160 extend through central opening 162 in siderail 20', and through an opening 168 in display 529 and in the siderail 20'. Conductors 160 may provide power and other signals to pendant display 529 from display 529 may provide signals through conductors 160 to the main bed control system. Connectors, such as screws or bolts or snap fittings 531 can be used to hold the display 529 to the siderail 20'. In some alternatives, the siderail 20' is an endboard or other board or component of the bed. Also, in some embodiments, the display 529 is mounted flush with the sideboard 20' or otherwise integrated therein. Additionally, the wires 160 may connect to the display via an electrical connector between display 529 and sideboard 20', such that an opening 168 in siderail 20' and display 529 is not needed. Wires may comprise individual wires or bundled wires such as on a ribbon connector. Siderail 20' (and the other siderails described herein) can locate the edge of the bed, can assist the patient and caregiver while the patient is in the bed, can impede the patient from moving off the bed, and can be moved up and down (deployed and stowed) as needed during use.

Figure 16:
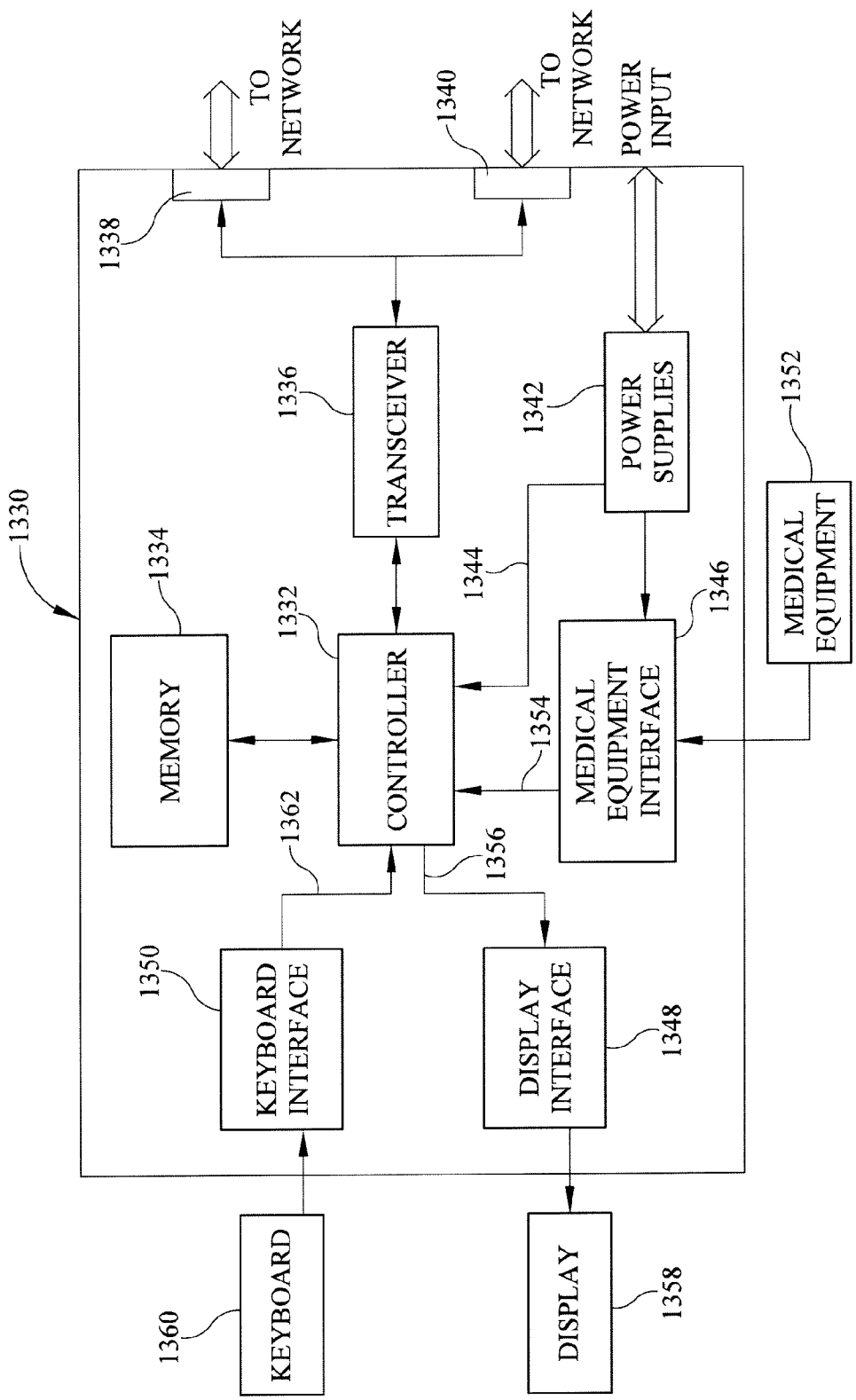
FIG. 16 is a block diagram of an illustrative embodiment of a bed control system having a medical equipment interface, according to principles of the present disclosure.

FIG. 16 illustrates a control system for a patient support system. The system 1330 includes a controller 1332 which can be a networking microprocessor. Controller 1332 accesses memory 1334 and can comprise one or more microprocessors, controllers, or control boards. Memory 1334 can include an EEPROM, and EPROM, and a static RAM. Controller 1332 is coupled to a RS-485 transceiver 1336. Transceiver 1336 is coupled to first and second network connectors 1338 and 1340. System 1330 includes an internal power supply 1342 coupled to a power input. Illustratively, power supply 1342 supplies a +5V supply voltage to controller 1332 on line 1344. Power supply 1342 also supplies power to a medical equipment interface 1346, a display interface 1348, and a keyboard interface 1350. Medical equipment interface 1346 receives an input from medical equipment, such as the patient vital monitors, patient therapy devices, or patient treatment devices discussed herein. An output of interface 1346 is coupled to controller 1332 on line 1354. Controller supplies information to display interface 1348 on line 1356. An output from display interface 1348 is coupled to a suitable display 1358. Keyboard interface 1350 receives an input from a keyboard 1360. An output of keyboard interface 1350 is coupled to controller 1332 by line 1362.

System 1330 provides a unified apparatus for controlling and monitoring bed functions as well as for controlling and/or monitoring functions of the medical equipment. Medical equipment 1352 and keyboard 1360 provide input devices for inputting information into system 1330. It is understood that any type of input device can be used. Information from system 1330 can be sent to the hospital network through transceiver 1336 and communication module 1020 or to another remote location via accessory module 1016. An output device such as display 1358 is provided to display information to the user. The display 1359 can be a series of LEDS or a display panel, such as a LCD display. Memory 1334 contains code that translates raw medical equipment information and keyboard input information from keyboard 1360 into specific data or commands, either for local on-bed use or for hospital network off-bed use. For instance, the nurse can take patient vitals using the medical equipment or input various information into keyboard 1360 related to the patient. This input can be used to generate an internal chart of the medical history of the patient for use on the hospital bed. This chart data can be displayed on display 1358. In addition, this chart can be transmitted over the hospital network or transmitted to a remote location using a data link coupled to accessory port 1016.

Another use of system 1330 is for inputting a control sequence used to control a bed control module to perform a dedicated function on the bed. For instance, a caregiver can prescribe a certain surface therapy for pulmonary or other type of treatment of the patient on the bed. This treatment prescription can specify a period of time for percussion and vibration therapy or for rotational therapy of the patient on the bed. The prescription can include a specific period of time for the therapy with varying rates of rotation or a varying frequency of percussion and vibration. This specific control sequence is input into system 1330. System 1330 then automatically executes the prescribed control sequence by transmitting appropriate commands at appropriate times through transceiver 1336 to the network and to the selected bed control modules to control the selected modules in the prescribed control sequence.

The patient support systems described herein can include any one or more of the features or systems described in Appendix A of U.S. Provisional Application Nos. 61/224,851 and 61/225,920 to which the present application claims benefit and/or in U.S. Provisional Patent Application Nos. 61/106,830 filed Oct. 20, 2008, 61/000,489 filed Oct. 26, 2007, and U.S. patent application Ser. No. 12/256,637 filed Oct. 23, 2008, the entire disclosures of which are hereby incorporated herein by reference.

The foregoing description of various embodiments and principles of the disclosure have been presented for the purposes of illustration and description. It is not intended to be exhaustive or to limit the disclosure to the precise forms disclosed. Many alternatives, modifications and variations will be apparent to those skilled in the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and broad scope of the various possible inventions disclosed herein and defined by the claims.

The invention claimed is:

1. A hospital bed comprising
a frame,
an inflatable mattress supported by the frame,
a plurality of siderails coupled to the frame,
a headboard coupled to the frame,
a footboard coupled to the frame,
a pneumatics system coupled to the frame, the pneumatics system operable to inflate the mattress and provide air to a respiratory therapy device and a sequential compression therapy device,
an on-bed physiologic monitor including electrodes attachable to a patient to sense at least one physiologic parameter of the patient supported by the frame,
bed electronics carried by the frame and configured to communicate with the physiologic monitor, the bed electronics comprising pneumatic system electronics that are integrated into the pneumatics system, and
a plurality of graphical displays coupled to the bed electronics, a first graphical display of the plurality of graphical displays being included as part of a first siderail of the plurality of siderails and a second graphical display of the plurality of graphical displays being included as part of one of the headboard and the footboard, each of the first and second graphical displays being operable to electronically display the physiologic parameter sensed by the physiologic monitor.

2. The hospital bed of claim 1, wherein the second graphical display is included as part of the headboard and faces away from the frame.

3. The hospital bed of claim 2, further comprising a third graphical display included as part of the headboard.

4. The hospital bed of claim 3, wherein the second graphical display displays data relating to a first physiologic parameter of the patient and the third graphical display displays data relating to a second physiologic parameter of the patient.

5. The hospital bed of claim 3, wherein the second and third graphical displays are located in spaced-apart, side-by-side relation.

6. The hospital bed of claim 1, wherein the second graphical display is included as part of the footboard and faces toward the frame.

7. The hospital bed of claim 6, further comprising a third graphical display included as part of the footboard.

8. The hospital bed of claim 7, wherein the second graphical display displays data relating to a first physiologic parameter of the patient and the third graphical display displays data relating to a second physiologic parameter of the patient.

9. The hospital bed of claim 7, wherein the second and third graphical displays are located in spaced-apart, side-by-side relation.

10. A hospital bed comprising
a frame,
an inflatable mattress supported by the frame,
a plurality of siderails coupled to the frame,
a headboard coupled to the frame,
a footboard coupled to the frame,
a pneumatics system coupled to the frame, the pneumatics system operable to inflate the mattress and provide air to a respiratory therapy device and a sequential compression therapy device,
an on-bed physiologic monitor including electrodes attachable to a patient to sense at least one physiologic parameter of the patient supported by the frame,
bed electronics carried by the frame and configured to communicate with the physiologic monitor and the pneumatics system, the bed electronics comprising pneumatic system electronics that are integrated into the pneumatics system, and
a plurality of graphical displays coupled to the bed electronics, a first graphical display of the plurality of graphical displays being included as part of a headboard and a second graphical display of the plurality of graphical displays being included as part of the footboard, wherein one of first and second graphical displays electronically shows information pertaining to one of the physiologic monitor and the pneumatics system, and wherein the other of the first and second graphical displays electronically shows information pertaining to the other of the physiologic monitor and the pneumatics system.

11. The hospital bed of claim 10, wherein the first graphical display shows data pertaining to the physiologic monitor and the second graphical display shows information pertaining to the pneumatics system.

12. The hospital bed of claim 10, wherein the respiratory therapy device comprises a respiratory therapy garment worn by a patient for high frequency chest wall oscillation therapy.

13. The hospital bed of claim 10, wherein the sequential compression therapy device comprises a sequential compression therapy sleeve worn by a patient for prevention of deep vein thrombosis.

14. The hospital bed of claim 10, further comprising a third graphical display included as part of a first siderail of the plurality of siderails, the third graphical display showing information pertaining to at least one of the physiologic monitor and the pneumatics system.

15. A hospital bed comprising
a frame;
an inflatable mattress supported by the frame;
a pneumatics system coupled to the frame, the pneumatics system operable to inflate the mattress and provide air to a respiratory therapy device and a sequential compression therapy device;
hospital bed electronics carried by the frame, the hospital bed electronics comprising pneumatic system electronics that are integrated into the pneumatics system, the hospital bed electronics controlling each of the following: movement of portions of the frame to reposition a patient, operation of an IV pump, operation of a vital signs monitor including electrodes attachable to the patient to sense at least one physiologic parameter of the patient, operation of the respiratory therapy device, and operation of the sequential compression therapy device;
at least one barrier coupled to the frame; and
at least one graphical display that is included as part of the barrier and that electronically displays information pertaining to operation of the IV pump, information pertaining to operation of the vital signs monitor, information pertaining to operation of the respiratory therapy device, and information pertaining to operation of the sequential compression therapy device.

16. The hospital bed of claim 15, further comprising user inputs carried by the barrier and usable to command the hospital bed electronics regarding control of the operation of the IV pump, the vital signs monitor, the respiratory therapy device, and the sequential compression therapy device.

17. The hospital bed of claim 15, wherein the respiratory therapy device comprises one of a respiratory therapy garment worn by a patient for high frequency chest wall oscillation therapy and the sequential compression therapy device comprises one of a sequential compression therapy sleeve worn by a patient for prevention of deep vein thrombosis.

18. The hospital bed of claim 15, wherein the hospital bed electronics communicates via wireless signals with at least one computer device that is spaced from the hospital bed.

19. The hospital bed of claim 15, wherein the hospital bed electronics includes a patient audio port to which a patient attaches a personal audio player.

20. The hospital bed of claim 15, wherein the hospital bed electronics is communicatively coupled via a hospital network to a medical records system and further comprising a keyboard coupled to the hospital bed electronics for entering patient vital signs information into a patient medical record via the hospital bed electronics.

* * * * *